US009937251B2

(12) United States Patent
Gazzinelli et al.

(10) Patent No.: US 9,937,251 B2
(45) Date of Patent: Apr. 10, 2018

(54) **UTILIZATION OF RECOMBINANT INFLUENZA VIRUSES AND MODIFIED VACCINIA ANKARA VIRUS (MVA) WITH GENES THAT ENCODE FOR THE *TOXOPLASMA GONDII* SAG1 AND SAG2 SURFACE PROTEINS, AS VACCINES AGAINST TOXOPLASMOSIS**

(75) Inventors: Ricardo Tostes Gazzinelli, Belo Horizonte (BR); Rafael Polidoro Alves Barbosa, Nova Floresta (BR); Braulia Costa Caetano, Belo Horizonte (BR); Alexandre de Magalhaes Vieira Machado, Belo Horizonte (BR); Oscar Bruna-Romero, Belo Horizonte (BR); Flavio Fonseca Guimaraes, Belo Horizonte (BR); Erica Araujo Mendes, Belo Horizonte (BR)

(73) Assignee: FUNDACAO OSWALDO CRUZ, Rio de Janeiro (BR)

( * ) Notice: Subject to any disclaimer, the term of this patent is extended or adjusted under 35 U.S.C. 154(b) by 1012 days.

(21) Appl. No.: 12/808,028

(22) PCT Filed: Dec. 22, 2008

(86) PCT No.: PCT/BR2008/000398
§ 371 (c)(1),
(2), (4) Date: Oct. 28, 2010

(87) PCT Pub. No.: WO2009/079731
PCT Pub. Date: Jul. 2, 2009

(65) Prior Publication Data
US 2011/0045016 A1    Feb. 24, 2011

(30) Foreign Application Priority Data

Dec. 21, 2007 (BR) .................................... 0704860

(51) Int. Cl.
*A61K 39/012*    (2006.01)
*A61K 39/00*    (2006.01)

(52) U.S. Cl.
CPC .... *A61K 39/012* (2013.01); *A61K 2039/5256* (2013.01); *A61K 2039/545* (2013.01); *C12N 2710/24143* (2013.01); *C12N 2760/16011* (2013.01)

(58) Field of Classification Search
None
See application file for complete search history.

(56) References Cited

U.S. PATENT DOCUMENTS

2003/0138454 A1    7/2003   Hill et al.

FOREIGN PATENT DOCUMENTS

WO        0191536 A2    12/2001
WO     2007051271 A2     5/2007

OTHER PUBLICATIONS

Roque-Resendiz et al., MVA ROP2 vaccinia virus recombinant as a vaccine candidate for toxoplasmosis, 2004, Parasitology, vol. 128, pp. 397-405.*
Woodland, Jump-starting the immune system: prime-boosting comes of age, 2004, Trends in Immunology, vol. 25, No. 2, pp. 98-104.*
Caetano et al., Vaccination with Replication-Deficient Recombinant Adenoviruses Encoding the Main Surface Antigens of *Toxoplasma gondii* Induces Immune Response and Protection Against Infection in Mice, 2006, Human Gene Therapy, vol. 17, pp. 415-426.*
International Search Report for PCT/BR2008/000398.
Wang, et al., Single Mucosal, but Not Parenteral, Immunization with Recombinant Adenoviral-Based Vaccine Provides Potent Protection fromPulmonary Tuberculosis, The Journal of Immunology, 2004, 173: 6357-6365.
Ricupito, et al., Booster Vaccinations against Cancer are Critical in Prophylactic but Detrimental in Therapeutic Settings, Cancer Res: 73(12); 1-10, 2013 American Association for Cancer Research.
Barbosa, et al, Vaccination using Recombinants Influenza and Adenoviruses Encoding Amastigote Surface Protein-2 are Highly Effective on Protection against Trypanosoma cruzi Infection, Apr. 2013, vol. 8, Issue 4, PLOS ONE www.plosone.org.
Schwartz, et al, Efficient homologous prime-boost strategies for T cell vaccination based on virus-like particles, Eur. J. Immunol. 2005, 35: 816-821.
Hammer, et al, Efficacy Trial of a DNA/rAd5 HIV-1 Preventive Vaccine, The New England Journal of Medicine, vol. 369, No. 22 Nov. 28, 2013.
Lemke, et al., Antigen-coated poly a-hydroxy acid based microparticles for heterologous prime-boost adenovirus based vaccinations, Biomaterials 34 (2013) 2524-2529.
Shih-Wen Lin, et al. Recombinant adeno-associated virus vectors induce functionally impaired transgene product-specific CD8+ cells in mice, The Journal of Clinical Investigation, vol. 117, Issue 12 (Dec. 3, 2007).
Li, S; Rodrigues, M; Rodriguez, D; Rodriguez, Jr; Esteban, M, Palese, P; et al. Priming with recombinant influenza virus followed by administration of recombinant vaccinia virus induces CD8+ T-cell-mediated protective immunity against malaria. Proceedings of the National Academy of Sciences of the United States of America, 90(11):5214-8, 1993.
Machado, AV; Caetano, BC; Barbosa, RP; Salgado, AP; Rabelo, RH; Garcia, CC; Bruna-Romero, O; Escriou, N; Gazzinelli, RT. Prime and boost immunization with influenza and adenovirus encoding the *Toxoplasma gondii* surface antigen 2 (SAG2) induces strong protective immunity. Vaccine, 28(2010):3247-3256, 2010.

* cited by examiner

Primary Examiner — Benjamin P Blumel
(74) Attorney, Agent, or Firm — Caesar Rivise, PC

(57) ABSTRACT

The present invention concerns to recombinant influenza viruses and modified Vaccinia Ankara viruses (MVA), and to a process for construction of recombinant influenza viruses and modified vaccinia Ankara viruses (MVA) with genes that encode for the *T. gondii* parasite SAG1 (MVA) and SAG2 (MVA and influenza) proteins, by means of a homologous recombination technique between two transfer vectors (for construction of MVA virus) and reverse genetics (for construction of influenza virus). Additionally, the present invention describes a vaccine composition using recombinant influenza viruses and modified vaccinia Ankara viruses (MVA), or recombinant adenoviruses and modified vaccinia Ankara viruses (MVA), for immunization against infections caused by the *T. gondii* parasite.

6 Claims, 15 Drawing Sheets

UTILIZATION OF RECOMBINANT INFLUENZA VIRUSES AND MODIFIED VACCINIA ANKARA VIRUS (MVA) WITH GENES THAT ENCODE FOR THE *TOXOPLASMA GONDII* SAG1 AND SAG2 SURFACE PROTEINS, AS VACCINES AGAINST TOXOPLASMOSIS

FIELD OF THE INVENTION

The present invention concerns to recombinant influenza viruses and modified Vaccinia Ankara viruses (MVA), and to a process for construction of recombinant influenza viruses and modified Vaccinia Ankara viruses (MVA) with genes that encode for the *T. gondii* parasite SAG1 (MVA) and SAG2 (MVA and influenza) proteins, by means of a homologous recombination technique between two transfer vectors (for construction of MVA virus) and reverse genetics (for construction of influenza virus). Additionally, the present invention describes a vaccine composition using recombinant influenza viruses and modified vaccinia Ankara viruses (MVA), or recombinant adenovirus and modified vaccinia Ankara viruses (MVA), for immunization against infections caused by the *T. gondii* parasite.

Finally, the present invention describes a novel immunization method against infections or tumoral diseases, using recombinant influenza virus and adenovirus, in heterologous protocols of immune response induction and enhancement.

BACKGROUND OF THE INVENTION

Toxoplasmosis is one of the most common zoonoses in various regions of the world, being caused by the *T. gondii* protozoa. It is estimated that nearly one third of the world's population has been exposed to this pathogen. In Brazil, the prevalence of infection by *T. gondii* varies from 50 to 80%, with the highest rates occurring in some of the Northern and Southern states, and the lowest values in the Southeast states [Orefice, F. & Bonfioli, A. A. (2000). Uveìte Clinica e Cirùrgica(Uveitis and Surgical Clinic). In toxoplasmosis), pp. 619-680. Edited by E. C. Médica, Rio de Janeiro].

The *T. gondii* has three infectious forms: the tachyzoites, which multiply rapidly inside the cells throughout the body, the bradyzoites, which have a slower multiplication rate and are found in intracellular cysts in various tissues, and the sporozoites, which are present in the oocysts released in feces of the definitive hosts [Rey, L. (1991). *Toxoplasma gondii* e toxoplasmosis. In *Parasitologia Humana*. (*Toxoplasma gondii* and toxoplasmosis. In Human Parasitology.), pp. 274-285. Rio de Janeiro: Guanabara Koogan.]

An important characteristic of the *T. gondii* infection is the tissue cysts formation, during the chronic phase of disease. Cysts are rounded intracellular structures, bounded by an elastic wall formed by material derived from the host cell and the parasite. The cysts develop with higher frequency in the brain, eyes, cardiac and skeletal striated muscle, although its distribution and quantity vary between different species of hosts [Dubey, J. (1997). Tissue cyst tropism in *Toxoplasma gondii*: a comparison of tissue cyst formation in organs of cats, and rodents fed oocysts. *Parasitology* 115.]

*T. gondii* has an asexual reproduction stage and a sexual reproduction stage. The latter occurs only in Felidae, which leads to description of these mammals as the parasite's definitive hosts. [Tenter, A. M., Heckreroth, A. R. & Weiss, L. M. (2000). *Toxoplasma gondii*: from animals to humans. *International Journal of Parasitology* 30, 1217-1258.] The infection of intermediate and definitive hosts can occur through ingestion of tissue cysts in meat or viscera, by ingestion of oocysts sporulated from environmental contamination by feces of definitive hosts or also by transplacental transmission of tachyzoites [Tenter et. al., 2000].

Most of the toxoplasmosis cases in humans are asymptomatic. However, the acute infections in prenatal stage or during pregnancy can result in major complications. At pregnancy beginning, toxoplasmosis can cause abortion, neonatal death and fetal abnormalities. In the last three decades, the incidence of prenatal infection has been estimated in the range of 1 to 100 per 10,000 births, in different countries.

Regarding chronic infections in immunocompromised individuals, a reactivation can occur, triggering a pathological picture of great seriousness. For example, we can mention encephalitis, pulmonary toxoplasmosis, and disseminated toxoplasmosis, which have been observed in patients with immunodeficiencies related to various diseases such as Hodgkin's disease and AIDS. It is estimated that 40% of AIDS patients develop encephalitis caused by *Toxoplasma*, being that 10 to 30% die as result of this infection [Ferreira, M. S. & Borges, A. S. (2002). Some aspects of protozoan infections in immunocompromised patients—a review. *Memórias do Instituto Oswaldo Cruz* 97, 443-457] [Tenter et al., 2000]

The disseminated toxoplasmosis can also be a complication arising from organs and bone marrow transplant. This may arise from both the transplant of organs from donors infected with *T. gondii* to a susceptible recipient, as from reactivation of latent infection in recipients, due to immunosuppressive therapy [Tenter et al, 2000].

Considerable effort has been applied for developing a vaccine that prevents the transmission of *T. gondii* within human and animal populations. The main objective of a vaccine against *T. gondii* is to generate an immune response in different hosts, controlling the parasite's replication and its transmission within the population. The induction of an immune response, prior to infection with the parasite, would prevent the release of oocysts by definitive hosts, preventing the formation of tissue cysts in intermediate hosts, and their oral transmission via meat, and would prevent the development of a state of asymptomatic carriers subject to a recall in humans. A vaccine could also prevent the acute toxoplasmosis in pregnant women and the transplacental transmission [Alexander, J., Jebbari, H., Bluethmann, H., Satoskar, A. & Roberts, C. W. (1996). Immunological control of *Toxoplasma gondii* and appropriate vaccine design. *Current Topics in Microbiology and Immunology: Toxoplasma gondii.*, 183-195].

Initial studies showed that it is possible to induce protective immunity, with activation of T $CD4^+$, T $CD8^+$ cells and production of IFN-γ, using attenuated forms of the parasite. However, vaccines produced this way are not suitable for application in humans, considering the risk of reversion of the vaccine samples to a pathogenic state [Gazzinelli, R. T., Hakim, F. T., Hieny, S., Shearer, G. M. & Sher, A. (1991). Synergistic role of CD4+ and CD8+ T lymphocytes in IFN-gamma production and protective immunity induced by an attenuated *Toxoplasma gondii* vaccine. *Journal of Immunology* 146, 286-292] [Hiramoto, R. M., Galisteo, A. J., Nascimento, N. & Andrade Jr, H. F. (2002). 200Gy sterilized *Toxoplasma gondii* tachyzoites maintain metabolic functions and mammalian cell invasion, eliciting cellular immunity and cytokine response similar to natural infection in mice. *Vaccine* 20, 2072-2081] [Rodrigues, M. M., Boscardin, S. B., Vasconcelos, J. R., Hiyane, M. I., Salay, G. &

Soares, I. S. (2003). Importance of CD8 T cell-mediated immune response during intracellular parasitic infections and its implications for the development of effective vaccines. *Annals of the Brazilian Academy of Sciences* 75, 443-468] [Sayles, P. & Johnson, L. L. (1996). Intact immune defenses are required for mice to resist the ts-4 vaccine strain of *Toxoplasma gondii*. *Infection & Immunity* 64, 3088-3092]. To bypass this problem, molecular biology techniques that allow the parasite genes cloning and expression has been used to develop the named subunit vaccine, containing only *T. gondii* immunogenic components. (Biemans et al., 1998, Büllow & Boothroyd, 1991). (Biemans et al., 1998, Bulow & Boothroyd, 1991).

Recently, significant progress has been made in identifying *T. gondii* antigens that can induce protective immune response. Most of the work has been focused on surface antigens expressed in tachyzoites, with particular interest in SAG1, SAG2 and SAGS, which act in the host cell invasion process [Lekutis, C., Fergunson, D. J. P., Grigg, M. E., Camps, M. & Boothroyd, J. C. (2001). Surface antigens of *Toxoplasma gondii*: variations on a theme. *International Journal of Parasitology* 67, 5869-5876]. The SAGs sequence are maintained within different strains of *T. gondii* and, moreover, these antigens stimulate cellular and humoral response, which makes these proteins good candidates for development of vaccines.

Amongst vectors for expression of these antigens, both in humans as in other animals, the recombinant viruses deserve mention [Rocha, C., Caetano, B., Machado, A. & Bruna-Romero, O. (2004). Recombinant viruses as tools to induce protective cellular immunity against infectious diseases. *International Microbiology* 7, 89-94] [Rodrigues et al., 2003]. Studies using different recombinant virus (vaccinia, adenovirus, Sindbis and influenza) expressing the *Plasmodium yoelii* antigens, showed that such viruses are capable of inducing a protective immunity in BALB/c mice exposed to an experimental infection by *P. yoelii* sporozoites [Li, S., Rodrigues, M., Rodriguez, D., Rodriguez, J. R., Esteban, M., Palese, P., Nussenzweig, R. S., Zavala, F. & Alexander, D. J. (1993b). Priming with recombinant influenza virus followed by administration of recombinant vaccinia virus induces CD8+ T-cell-mediated protective immunity against malaria. *Proceedings of the National Academy of Sciences of the United States of America* 90, 5214-8] [Rodrigues, M., Li, S., Murata, K., Rodriguez, D., Rodriguez, J. R., Bacik, I., Bennink, J. R., Yewdell, J. W., Garcia-Sastre, A. & Nussenzweig, R. S. (1994). Influenza and vaccinia viruses expressing malaria CD8+ T and B cell epitopes. Comparison of their immunogenicity and capacity to induce protective immunity. *Journal of Immunology* 153, 4636-48] [Tsuji, M., Bergmann, C., Takita-Sonoda, Y., Murata, K., Rodrigues, E., Nussenzweig, R. & Zavala, F. (1998). Recombinant Sindbis viruses expressing a cytotoxic T-lymphocyte epitope of a malaria parasite or of influenza virus elicit protection against the corresponding pathogen in mice. Journal of Virology 72, 6907-6910].

Most of the experimental data obtained so far showed that, when the viral vectors are used alone, the protection level achieved was significantly lower than that observed when two different viral vectors expressing the same antigen were used for prime and boost immunization. [Gherardi, M. M., Najera, J. L., Perez-Jimenez, E., Guerra, S., Garcia-Sastre, A. & Esteban, M. (2003). Prime-boost immunization schedules based on influenza virus and vaccinia virus vectors potentiate cellular immune responses against human immunodeficiency virus Env protein systemically and in the genitorectal draining lymph nodes. *Journal of Virology* 77, 7048-7057] [Li, S., Polonis, V., Isobe, H., Zaghouani, H., Guinea, R., Moran, T., Bona, C. & Palese, P. (1993a). Chimeric influenza virus induces neutralizing antibodies and cytotoxic T cells against human immunodeficiency virus type 1. *Journal of Virology* 67, 6659-66] [Murata, K., Garcia-Sastre, A., Tsuji, M., Rodrigues, M., Rodriguez, D., Rodriguez, J. R., Nussenzweig, R. S., Palese, P., Esteban, M. & Zavala, F. (1996). Characterization of in vivo primary and secondary CD8+ T cell responses induced by recombinant influenza and vaccinia viruses. *Cellular Immunology* 173, 96-107] [Shiver, J. W., Fu, T. M., Chen, L., Casimiro, D. R., Davies, M. E., Evans, R. K., Zhang, Z. Q., Simon, A. J., Trigona, W. L., Dubey, S. A., Huang, L., Harris, V. A., Long, R. S., Liang, X., Handt, L., Schleif, W. A., Zhu, L., Freed, D. C., Persaud, N. V., Guan, L., Punt, K. S., Tang, A., Chen, M., Wilson, K. A., Collins, K. B., Heidecker, G. J., Fernandez, V. R., Perry, H. C., Joyce, J. G., Grimm, K. M., Cook, J. C., Keller, P. M., Kresock, D. S., Mach, H., Troutman, R. D., Isopi, L. A., Williams, D. M., Xu, Z., Bohannon, K. E., Volkin, D. B., Montefiori, D. C., Miura, A., Krivulka, G. R., Lifton, M. A., Kuroda, M. J., Schmitz, J. E., Letvin, N. L., Caulfield, M. J., Bett, A. J., Youil, R., Kaslow, D. C. & Emini, E. A. (2002). Replication-incompetent adenoviral vaccine vector elicits effective anti-immunodeficiency-virus immunity. Nature 415, 331-5].

This kind of immunization strategy is known as heterologous system for priming and boosting the immune response. As an example on the effectiveness of this strategy, we could mention the total inhibition of development of hepatic forms and 100% protection against malaria, in mice that were first immunized with recombinant adenovirus expressing the *P. yoelii* or *P. berghei* CS protein and boosted with a vaccinia virus expressing this same protein [Bruna-Romero, O., Gonzalez-Aseguinolaza, G., Hafalla, J. C., Tsuji, M. & Nussenzweig, R. S. (2001). Complete, long-lasting protection against malaria of mice primed and boosted with two distinct viral vectors expressing the same plasmodial antigen. *Proceeding of National Academy of Sciences of United States of America* 98, 11491-11496] [Gilbert, S. C., Schneider, J., Hannan, C. M., Hu, J. T., Plebanski, M., Sinden, R. & Hill, A. V. (2002). Enhanced CD8 T cell immunogenicity and protective efficacy in a mouse malaria model using a recombinant adenoviral vaccine in heterologous prime-boost immunization regimes. Vaccine 20, 1039-1045].

Amongst viruses potentially usable as antigens delivery vectors, the adenoviruses, the modified vaccinia Ankara viruses (MVA) and the influenza viruses have some characteristics making them interesting candidates for use in induction of a heterospecific immune response against *T. gondii* and other pathogens [Garcia-Sastre, A. (2000). Transfectant influenza viruses as antigen delivery vectors. *Advances in Virus Research* 55, 579-97] [Rocha et al., 2004] [Tatsis, N. & Ertl, H. C. (2004). Adenoviruses as vaccine vectors. *Molecular Therapy* 10, 616-629].

Amongst advantages of using the influenza virus, we could mention the fact that it does not integrate in the host genome and does not persist in the body. Furthermore, the existence of different influenza virus variants and subtypes enables the execution of sequential immunizations using two subtypes or variants of this virus [Ferko, B., Stasakova, J., Sereinig, S., Romanova, J., Katinger, D., Niebler, B., Katinger, H. & Egorov, A. (2001). Hyperattenuated recombinant influenza A virus nonstructural-protein-encoding vectors induce human immunodeficiency virus type 1 Nef-specific systemic and mucosal immune responses in mice. *Journal of Virology* 75, 8899-908]. Another favorable argument for choosing the influenza virus as vector for expression of heterologous sequences consists in that currently the molecular biology techniques for genetic manipulation of this virus are already well developed [Neumann, G. & Kawaoka, Y. (2002). Generation of influenza A virus from cloned cDNAs—historical perspective and outlook for the new millennium. *Reviews in Medical Virology* 12, 13-30] [Neumann, G. & Kawaoka, Y. (2004). Reverse genetics systems for the generation of segmented negative-sense RNA viruses entirely from cloned cDNA. *Current Topics in Microbiology and Immunology* 283, 43-60] and different strategies already exist for expression of heterologous proteins using recombinant influenza viruses. [Garcia-Sastre et al., 1994] [Machado, A., Naffakh, N., van der Werf, S. & Escriou, N. (2003). Expression of a foreign gene by stable recombinant influenza viruses harboring a dicistronic genomic segment with an internal promoter. *Virology* 313, 235-249] [Percy, N., Barclay, W. S., Garcia Sastre, A. & Palese, P. (1994). Expression of a foreign protein by influenza A virus. *Journal of Virology* 68, 4486-4492] [Takasuda, N., Enami, S., Itamura, T. & Takemori (2002). Intranasal inoculation of a recombinant influenza virus containing exogenous nucleotides in the NS segment induces mucosal immune response against the exogenous gene product in mice. *Vaccine* 20, 1579-1585] [Watanabe, T., Watanabe, S., Noda, T., Fujii, Y. & Kawaoka, Y. (2003). Exploitation of nucleic acid packaging signals to generate a novel influenza virus-based vector stably expressing two foreign genes. *Journal of Virology* 77, 10575-83].

Additional to the advantages above mentioned, is the ability of this of vector type to induce an heterospecific immune response, both local as systemic [Garulli, B., Kawaoka, Y. & Castrucci, M., R. (2004). Mucosal and systemic immune responses to a human immunodeficiency virus type 1 epitope induced upon vaginal infection with a recombinant influenza A virus. *Journal of Virology* 78, 1020-1025] [Gherardi, M. M., Najera, J. L., Perez-Jimenez, E., Guerra, S., Garcia-Sastre, A. & Esteban, M. (2003). Prime-boost immunization schedules based on influenza virus and vaccinia virus vectors potentiate cellular immune responses against human immunodeficiency virus Env protein systemically and in the genitorectal draining lymph nodes. *Journal of Virology* 77, 7048-7057]. The existence of a well-developed technology for influenza virus industrial scale production and the existence of attenuated viral strains are additional favorable points in using this vector. Regarding the attenuated strains, their use in humans has been authorized in the United States and they could then be used to construct recombinant live vaccines, able to immunize simultaneously against the influenza virus and some other pathogen [Izurieta, H. S., Haber, P., Wise, R. P., Iskander, J., Pratt, D., Mink, C., Chang, S., Braun, M. M. & Ball, R. (2005). Adverse events reported following live, cold-adapted, intranasal influenza vaccine. *Jama* 294, 2720-5] [Subbarao, K. & Katz, J. M. (2004). Influenza vaccines generated by reverse genetics. *Curr Top Microbiol Immunol* 283, 313-42].

Adenoviruses, in turn, are genetically stable, easy to handle and possess a remarkable capacity for heterologous sequences expression. Adenoviruses are still characterized by multiplying well in cellular culture and having broad tropism, being able to infect a wide range of cell types (replicating and non-replicating ones) and tissues. Moreover, they can be inoculated both by systemic and mucous routes.

Another favorable aspect of adenoviral vectors consists in that they are relatively safe, since they do not integrate in the host cells chromosomes [Tatsis & Ertl, 2004], and in that diseases caused by serotypes that normally infect humans are of little significance. Moreover, it is possible deleting significant portions of the viral genome, resulting in defective vectors for replication. This contributes not only to further enhance the security of this type of vector, but also to allow a better heterologous antigen expression [Xiang, Z. & Ertl, H. C. (1999). Induction of mucosal immunity with a replication-defective adenoviral recombinant. *Vaccine* 17, 2003-2008] [Xiang, Z. Q., Yang, Y., Wilson, J. M. & Ertl, H. C. (1996). A replication-defective human adenovirus recombinant serves as a highly efficacious vaccine carrier. *Virology* 219, 220-227].

Another interesting aspect of adenoviruses is the ability to change their cellular tropism by modifying the protein responsible for the virus adherence to host cells [Tatsis & Ertl, 2004]. Finally, it is possible using adenoviral vectors based on serotypes of low circulation in human population, or even non-human serotypes [Barouch, D. H., Pau, M. G., Custers, J. H., Koudstaal, W., Kostense, S., Havenga, M. J., Truitt, D. M., Sumida, S. M., Kishko, M. G., Arthur, J. C., Korioth-Schmitz, B., Newberg, M. H., Gorgone, D. A., Lifton, M. A., Panicali, D. L., Nabel, G. J., Letvin, N. L. & Goudsmit, J. (2004). Immunogenicity of recombinant adenovirus serotype 35 vaccine in the presence of pre-existing anti-Ad5 immunity. *Journal Immunology* 172, 6290-6297] [Farina, S. F., Gao, G. P., Xiang, Z. Q., Rux, J. J., Burnett, R. M., Alvira, M. R., Marsh, J., Ertl, H. C. & Wilson, J. M. (2001). Replication-defective vector based on a chimpanzee adenovirus. *Journal of Virology* 75, 11603-11613] [Fitzgerald, J., Gao, G., Reyes-Sandoval, A., Pavlakis, G., Xiang, Z., Wlazlo, A., Giles-Davis, W., Wilson, J. & Ertl, H. (2003). A simian replication-defective adenoviral recombinant vaccine to HIV-1 gag. *Journal Immunology* 170, 1416-1422] [Reyes-Sandoval, A., Fitzgerald, J. C., Grant, R., Roy, S., Xiang, Z. Q., Li, Y., Gao, G. P., Wilson, J. M. & Ertl, H. C. (2004). Human immunodeficiency virus type 1-specific immune responses in primates upon sequential immunization with adenoviral vaccine carriers of human and simian serotypes. *Journal of Virology* 78, 7392-7399], thus, allowing to bypass potential problems related to occurrence of a pre-existing immune response against the adenoviral vector.

Historically, the MVA (from "modified vaccinia virus Ankara) was created to serve as a safe vaccine against smallpox. This virus was attenuated after more than 570 passages on primary chicken embryo fibroblasts (CEF) cultures, during which occurred the deletion of several of the vaccinia virus genes responsible for virulence, rendering them unable to generate productive infections in mammals cells [Sutter, G. & Staib, C. (2003). Vaccinia vectors as candidate vaccines: the development of modified vaccinia virus Ankara for antigen delivery. *Curr Drug Targets Infect Disord* 3, 263-71]. The MVA viruses have the following advantages concerning its use as vaccine vectors:

(1) Ability to receive the insertion of large exogenous DNA sequences (up to 25 kb).
(2) Stability to freezing and freeze-drying.
(3) Lack of integration in the host genome due to the fact that this virus multiplies in the infected cells cytoplasm.
(4) Ability to induce cellular and humoral immune response against the heterologous antigen [Rocha et al., 2004].

BRIEF DESCRIPTION OF DRAWINGS

FIG. 1 shows the outline of cloning the SAG2 fragment in the pPRNA38-SAG2 plasmid.

FIG. 2 shows the strategy of construction of recombinant influenza viruses by reverse genetics.

FIG. 3A outlines the replication of a bicistronic segment of an influenza virus that contains the duplication of the 3' non-encoding region.

FIG. 3B shows the results of the experiment conducted using the Northern blot technique, whose purpose was the detection of different molecular species of viral RNA containing the coding sequence of the protein SAG2 in MDCK cells infected by recombinant influenza viruses (vNA38-SAG2).

FIG. 4A outlines the cloning of the SAG1 and SAG2 sequences in the pLW44 plasmid.

Figure 9:
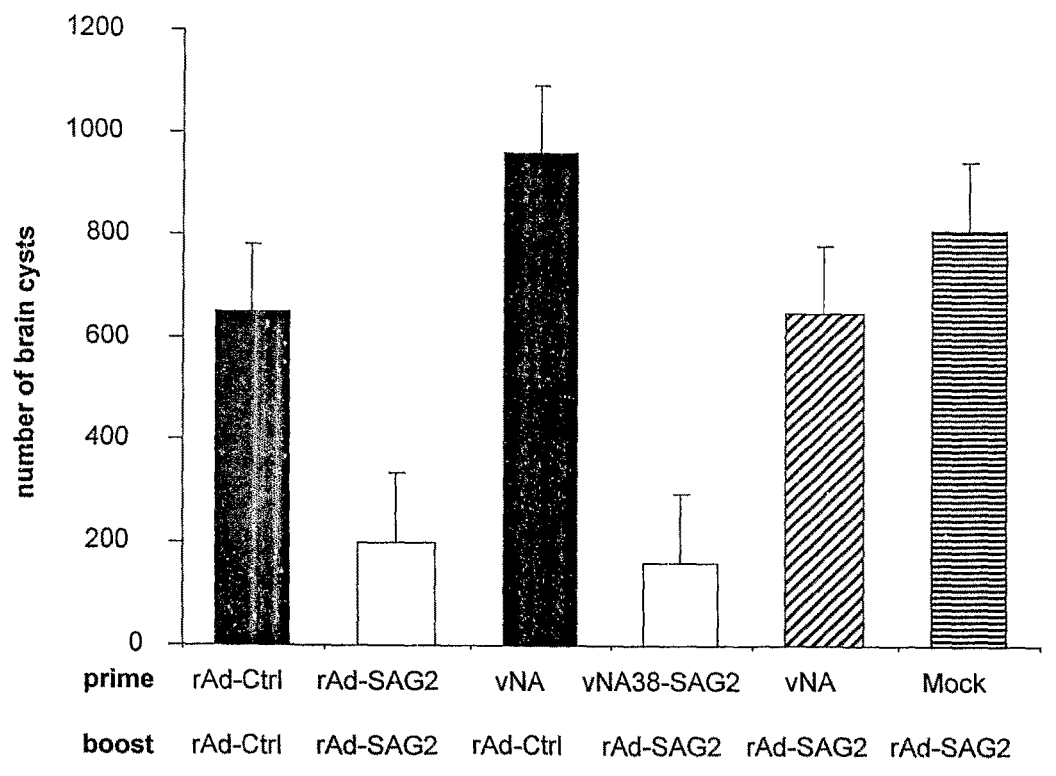

FIG. 9 shows the result of BALB/c mice immunized with recombinant viruses and challenged with *Toxoplasma gondii* PBR strain cysts, by oral route.

FIG. 15 shows the anti-SAG2 immune response in mice immunized according to the heterologous protocol of immune response induction and enhancement.

SUMMARY OF THE INVENTION

Figure 1:
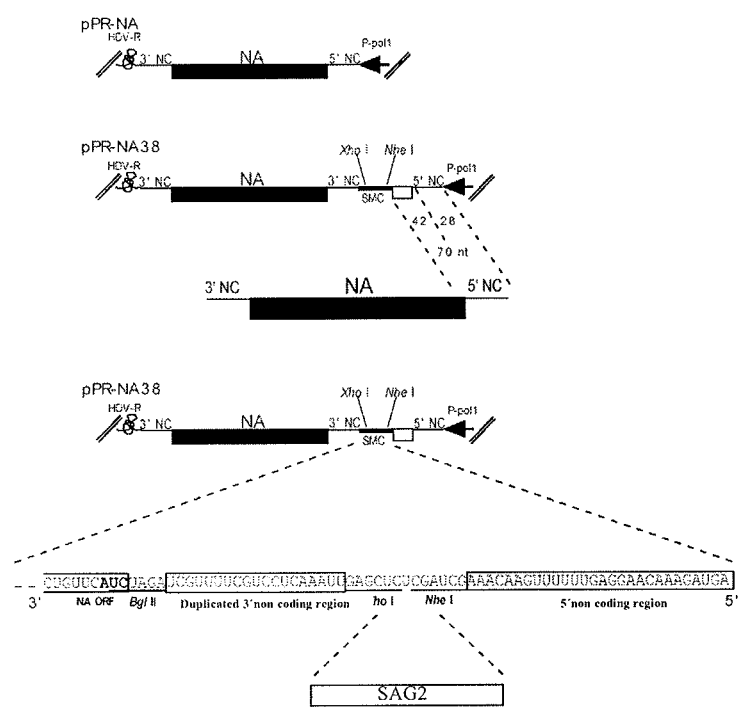

In its broadest concept, the invention presents the construction of the recombinant influenza viruses and modified vaccinia Ankara viruses (MVA) carrying the genes that encode for the SAG1 (MVA) and SAG2 (MVA and influenza) proteins of the *T. gondii* RH strain.

The invention also presents an immunization method against toxoplasmosis, using adenovirus and modified vaccinia Ankara virus (MVA), in heterologous protocols of immune response induction and enhancement.

The invention also presents an immunization method against toxoplasmosis, using recombinant influenza viruses and modified vaccinia Ankara viruses, in heterologous protocols of immune response induction and enhancement.

Finally, the invention describes a novel immunization protocol, using recombinant influenza virus and adenovirus, in heterologous protocols of immune response induction and enhancement, and aiming the development of vaccines against infectious or neoplasic diseases.

The first objective of the present invention is the construction of both recombinant influenza viruses carrying genes that encode for the *T. gondii* SAG2 proteins, and recombinant the MVA viruses with genes that encode for the *T. gondii* SAG1 or SAG2 proteins.

Another objective of the invention refers to a construction process, by reverse genetics technique, of a recombinant influenza virus with the gene that encodes the *T. gondii* SAG2 protein, as well as the construction of recombinant MVAs that encode the SAG1 and SAG2 *T. gondii* proteins, by means of the homologous recombination technique between the wild MVA and a transfer vector containing the genes that encode the mentioned proteins.

Another objective of the invention is presenting the composition of vaccines using recombinant viruses carrying *T. gondii* antigens, in heterologous immunization protocols, according to the following combinations: influenza and adenovirus, adenovirus and MVA or influenza and MVA.

Finally, another objective of the invention is presenting the composition of a vaccine against infectious or tumoral diseases, using recombinant influenza virus and adenovirus, in heterologous protocols of immune response induction and enhancement.

DETAILED DESCRIPTION OF THE INVENTION

The present concretization describes a construction process of recombinant MVA viruses carrying the genes that encode for the *T. gondii* RH strain SAG1 and SAG2 proteins. The present concretization also describes a construction process of recombinant influenza viruses carrying the gene that encodes the *T. gondii* RH strain SAG2 protein.

The construction process of recombinant influenza viruses occurs by means of reverse genetics technique, as presented hereunder.

Plasmids

Plasmid encoding a segment of modified influenza virus. This modification consists in the construction of a bicistronic segment, by insertion of a duplication of the 3' non-encoding region of such segment, followed by the insertion of a multiple cloning site, the duplication of the last nucleotides of the encoding region of the respective viral segment and of the 5' non-encoding region. The number of nucleotides of the encoding region that were duplicated and inserted between the multiple cloning site and the 5' non-encoding region varies according to the influenza virus segment to be modified. Such bicistronic segment remains inserted in the plasmid within the human polymerase I promoter (or any other primate) and the ribozyme sequence of hepatitis delta virus (or the termination site of the murine or human polymerase I promoter).

Plasmids encoding the remaining seven segments of the influenza virus, under control of the human polymerase I promoter (or any other primate) and the ribozyme sequence of hepatitis virus (or the termination site of the murine or human polymerase I promoter).

Plasmids encoding the replication complex proteins (PA, PB1 and PB2) and the nucleoprotein (NP) of the influenza virus.

In the present concretization, the pPRNA38-SAG2 plasmid was used as transfer plasmid. This plasmid contains a bicistronic segment of the A/WSN/33 (H1N1) virus neuraminidase (NA) segment. The neuraminidase segment was modified by insertion of a duplication of the 3' non-encoding region of such segment, followed by insertion of a cloning site recognized by the NheI and XhoI restriction enzymes, the duplication of the last 39 nucleotides of the encoding region and the termination codon of the neuraminidase and of the complete 5' non-encoding region. The encoding sequence of the *T. gondii* SAG2 protein was inserted at level of the NheI and XhoI cloning site.

In the present concretization, the pPRNA plasmid, which encodes the wild neuraminidase segment of the WSN virus was used as control.

In the present concretization, the pPOLI-NP, pPOLI-PA, pPOL1-PB1, pPOL1-PB2, pPOLI-HA, pPOLI-NS and pPOLI-M plasmids were used for transcription of the RNAs corresponding to the other 7 segments of the influenza virus.

In the present concretization, the pcDNA-NP, pcDNA-PA, pcDNA-PB1 and pcDNA-PB2 plasmids were used for expression of the influenza virus replication complex proteins. These plasmids carry the genes encoding the replication complex proteins (PA, PB1 and PB2) and the influenza virus nucleoprotein (NP) under control of the cytomegalovirus polymerase II promoter and the bovine growth hormone polyadenylation site.

In the generation process of recombinant influenza viruses, co-cultures of 293T and MDCK cells were transfected by the plasmids above. The 293T cells are very permissive to transfection. Inside the transfected cells, occur the transcription, replication and synthesis of all viral proteins and, consequently, the production of new virions. The MDCK cells present in co-culture are more permissive to the multiplication of influenza viruses and thus allow the amplification of the viruses generated from the transfection of 293T cells.

FIG. 1 outlines the construction process of the pPRNA38-SAG2 plasmid, which contains a bicistronic segment of the neuraminidase and the SAG2 protein encoding heterologous sequence. The pPR-NA35 plasmid derives from pPR-NA plasmid, which contains the complete cDNA segment of the NA in negative orientation, under control of the truncated human polymerase I promoter. This plasmid contains the cDNA of the recombinant segment of the NA in negative orientation, in which the NA ORF is followed by the duplication of the 3' promoter, by an XhoI/NheI cloning site, and by the original 5' promoter. The pPR-NA38 plasmid derives from the pPR-NA35 plasmid. This plasmid was constructed to preserve the integrity of the 5' termination over its last 70 nucleotides. This was achieved by insertion of a duplication of the last 39 nucleotides of the ORF and of the termination codon of the NA (white square in FIG. 1), which were inserted between the 5' promoter and the XhoI/NheI "linker". The sequence that encodes the *T. gondii* SAG2 protein was inserted in negative orientation between the sites recognized by the XhoI and NheI enzymes. The plasmid so obtained was named pPRNA38-SAG2.

Figure 2:
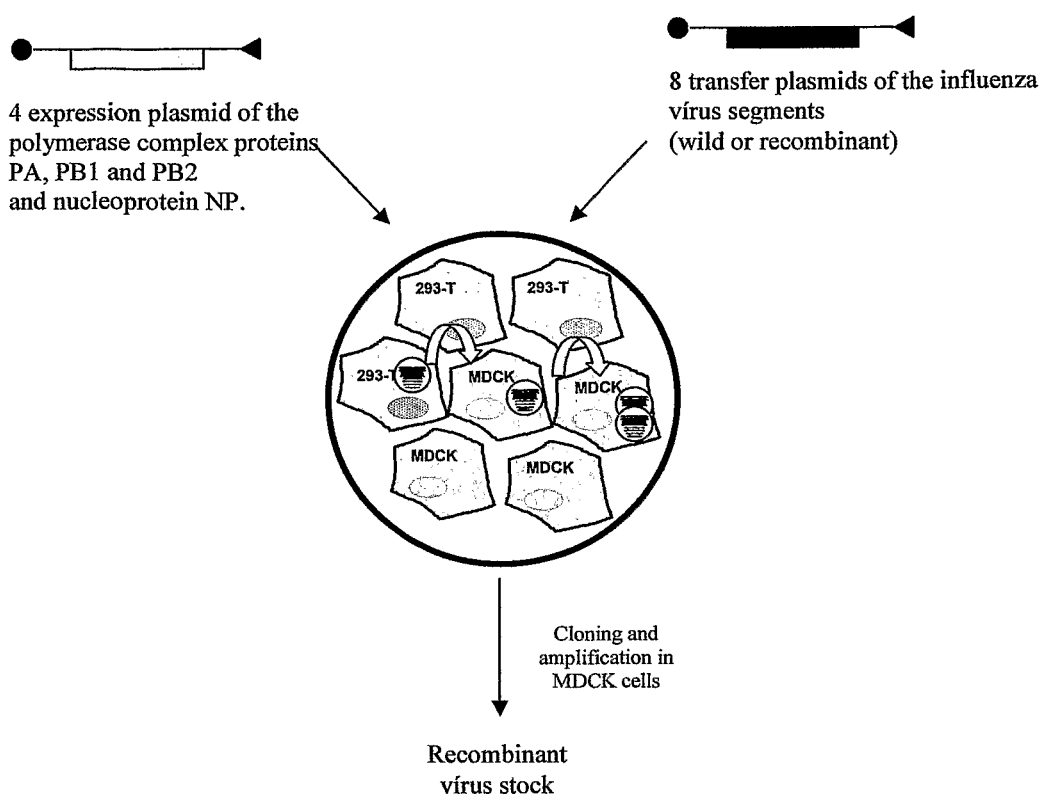

FIG. 2 outlines the construction process of the recombinant influenza viruses, by the helper virus free reverse genetics technique. Mentioned construction process of recombinant viruses comprises the following stages:
    cloning of the *T. gondii* gene that encodes the SAG2 protein in the pPRNA38 transfer vector;
    co-transfection of the wild segment transfer plasmid or neuraminidase bicistronic, of the transfer plasmids of the influenza virus other segments, and of the plasmids encoding the influenza viruses replication proteins;
    generation of influenza viruses by reverse genetics;
    cloning and amplification of the recombinant viruses.

The recombinant influenza viruses were obtained by reverse genetics according to methodology described by the P. Palese and G. Brownlee teams. As per FIG. 2, co-cultures of HEK 293T cells ($4\times10^5$ cells in 35 mm$^2$ plates) and MDCK cells ($3\times10^5$ cells in 35 mm$^2$ plates) were co-transfected with the pPR-NA plasmid or one of its derived plasmids (500 ng), by each of the plasmids that encode the other influenza virus segments (500 ng of each plasmid), and by the plasmids that allow the expression of the polymerase complex proteins (PA, PB1 and PB2: 500 ng each) and of the nucleoprotein NP (500 ng), in 10 µl of Fugene 6 (Roche), enabling the reconstitution of 8 functional ribonucleoproteic complexes in vivo and, in this way, the transcription and replication of the viral segments. The supernatants are collected 72 hours after transfection. After a stage of amplification in MDCK cells, the transfectant viruses are cloned and then amplified in MDCK cells.

Figure 3:
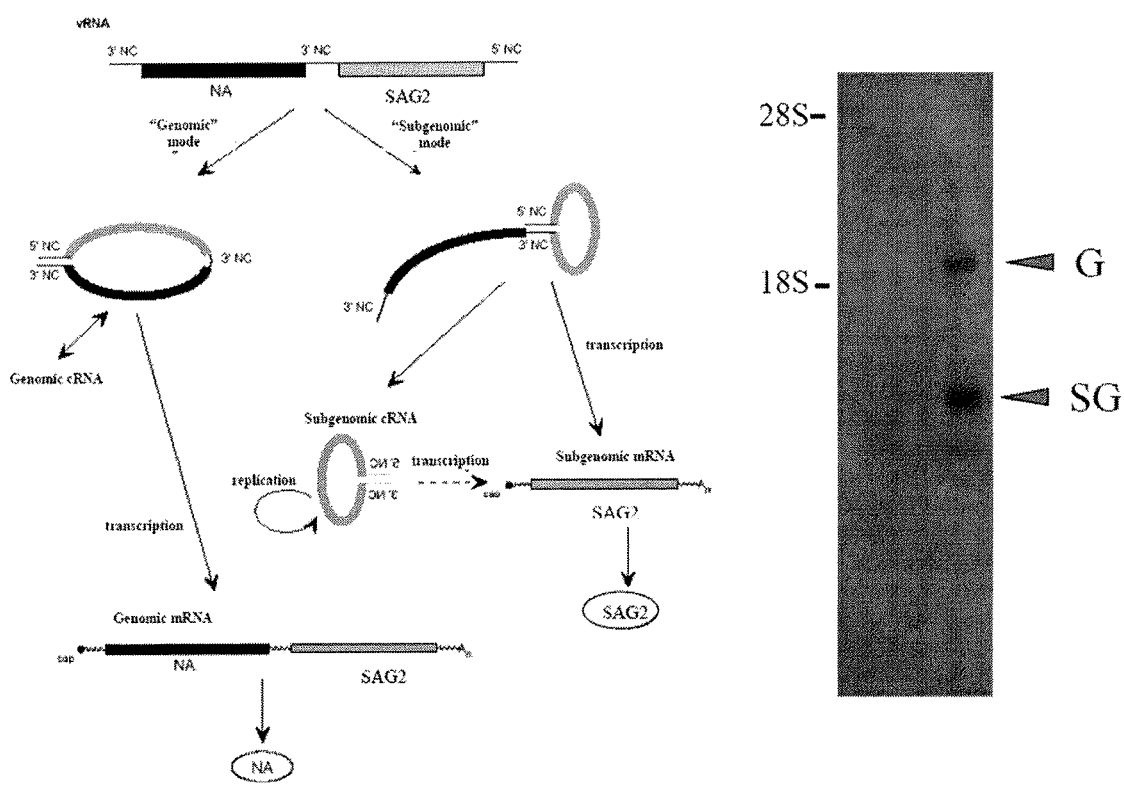

FIG. 3A shows the replication scheme of the neuraminidase bicistronic segment, and FIG. 3B shows the result of the northern blot experiment conducted on cells infected by the vNA38-SAG2 or vNA (control) viruses. In the channel for the RNA cells infected with the vNA38-SAG2 virus, it is possible to detect the presence of two molecular species: 1) One genomic RNA of greater size, containing both the neuraminidase and the SAG2 sequences and 2) One subgenomic RNA of smaller size, containing only the SAG2 encoding sequence.

In the cloning stage (FIG. 1), the gene that encodes the SAG2 protein was obtained by digestion with HindIII and BglII restriction enzymes, from the pCMV-link-SAG2 plasmid. The pPRNA38 vector was digested with the XhoI restriction enzyme.

The digestion products were treated with Klenow enzyme for filling-in the ends generated by digestion with restriction enzymes, producing "blunt ended" fragments.

The pPRNA38 vector had its ends dephosphorylated by treatment with SAP phosphatase enzyme.

The pPRNA38 vector and the digestion fragment containing the SAG2 protein encoding sequence were purified by agarose gel electrophoresis, at near 1%, and the gel bands corresponding to each gene were eluted from gel fragments by using a commercial purification kit.

After the purification procedure, linking reactions were performed amongst the digestion reaction products with an appropriate enzyme, in order to maintain preferably an insert/plasmid molar ratio of 3:1 and using, for example, the T4-ligase enzyme, by using preferably 10 units of enzyme per reaction. The linking reaction was maintained at approximately 16° C. temperature, for nearly 18 hours.

The products of the linking reaction were employed in *Escherichia coli* bacterium transformation. In the present concretization, the chemocompetent XLI-Blue strain of *Escherichia coli* bacterium was used.

The transformant bacteria were grown in appropriate culture containing an appropriate culture medium, such as LB medium. Approximately 100 µg/ml of ampicillin was added to the LB medium. Preferably, the mentioned culture occurred in a 16-18 hours period and the recombinant plasmids were purified with commercial plasmid isolation kits. The plasmids may alternatively be purified through alkaline lysis of the recombinant bacteria, with buffer containing sodium hydroxide and sodium dodecyl sulfate, followed by neutralization of bacterial lysate, with buffer composed of glacial acetic acid and potassium acetate, and subsequent filtration of lysate and precipitation of plasmids with 100% Ethanol.

The SAG2 gene was cloned in an oriented way, in the pPRNA38 plasmid. The presence of the recombinant gene was confirmed by observing the digestion profile of the purified plasmid.

For the reverse genetics and the recombinant influenza viruses construction, procedure used in the present invention was the method of simultaneous transfection of 12 plasmids, through Fugene reagent (Roche), over monolayers containing 293T and MDCK cells co-cultures. For generation of the recombinant influenza viruses with the SAG2 gene (vNA38-SAG2), the pPOLI-NP, PA, PB1, PB2, M, NS and HA plasmids, the pcDNA-NP, PA, PB1 and PB2 plasmids, and the pPRNA38-SAG2 plasmid were co-transfected. In the present description, it was used also the pPR-NA plasmid, which encodes the wild segment of the WSN virus neuraminidase. This plasmid was used in alternation with the pPRNA38-SAG2 plasmid, as a positive control of the reverse genetics experiments.

For the transfection (co-transfection) to occur, the execution of a first procedure was required for preparing the permissive cells. During this first procedure for permissive cells preparation as, for example, the HEK293T and MDCK cells, the same were seeded preferably into six-well plates, in a density of approximately 400,000 and 300,000 cells/well of HEK293T and MDCK respectively. To each well were added nearly 2 ml/well of HEK293T and MDCK cells. Mentioned cells were cultured during nearly 24 hours, under a preferred temperature of 37° C., in an atmosphere with nearly 5% $CO_2$, of an appropriate culture medium as, for example, the DMEM medium, which was supplemented with approximately 5% fetal bovine serum, sodium bicarbonate in a preferred concentration of 5 mM, HEPES in a preferred concentration of 25 mM and nearly 40 mg/1 of gentamicin. Mentioned culture medium is called complete DMEM medium.

For generation of the recombinant vNA38-SAG2 influenza virus and the wild WSN virus (vNA; positive control), at least one co-transfection reaction was performed. Each co-transfection reaction was performed into an individual well of a six-well plate, containing a monolayer of nearly 700,000 cells.

Until the moment of addition of the transfection reagents and the plasmids, the six-well plates containing washed monolayers were maintained in culture with nearly 2 ml/well of complete DMEM medium, at a preferred temperature of 37° C. and 5% $CO_2$ atmosphere.

For generation of the influenza viruses, the following transfection reaction was prepared for each 35 mm² plate: approximately 500 ng of each of the plasmids were diluted in a solution containing 10 µl of Fugene transfection reagent and 90 µl of complete DMEM medium with no fetal bovine serum.

The mentioned Fugene+DMEM mixture was prepared by addition of 10 µl of Fugene transfection reagent and 90 µl of complete DMEM medium with no fetal bovine serum, followed by incubation of the mixture during 5 minutes at room temperature.

The Fugene+DMEM mixture was added to the plasmids mixture and incubated during 15 minutes at room temperature, and then added to the wells containing the MDCK and 293T cells co-culture.

After transfection of the transfection reagent and the plasmids, the six-well plates containing the washed monolayers were maintained in culture with nearly 2 ml of complete DMEM medium supplemented with 10% FBS/well, at a preferred temperature of 35° C. and 5% $CO_2$ atmosphere during 24 hours. After this time, the culture medium was removed and replaced by 2 ml of complete DMEM medium, supplemented with 2% FBS/well. The cells were incubated during additional 48 hours at 35° C. and 5% $CO_2$ atmosphere.

72 hours after transfection, the supernatants of the cellular cultures were collected and clarified by centrifugation, during 10 minutes, at 3,000 rpm and 4° C. The clarified supernatants were aliquoted and then stored at −70° C., for latter amplification of the infectious titer of the influenza virus generated by reverse genetics.

The amplification of the influenza viruses obtained by reverse genetics was performed on monolayers of MDCK cells in 25 cm² culture flasks ($1.5 \times 10^6$ cells per flask) and cultured in 4 ml of complete DMEM medium supplemented with 5% FBS. For this purpose, the culture medium was removed and the monolayers were washed with 3 ml of complete DMEM medium with no FBS.

The monolayers were infected with 500 µl of supernatant of reverse genetics. After one hour of incubation, the monolayers were covered with complete DMEM culture medium, supplemented with 2% FBS, being 2 ml the culture final volume. The cells were incubated during additional 72 hours at 35° C. and 5% $CO_2$ atmosphere.

72 hours after infection, the supernatants of the cellular cultures were collected and clarified by centrifugation, during 10 minutes, at 3,000 rpm and 4° C. The clarified supernatants were aliquoted and then stored at −70° C. for latter cloning of the recombinant viruses.

The recombinant influenza viruses were cloned by the lysis plate under agarose cloning technique. For this purpose, the viral stocks were subjected to serial decimal dilutions, in complete DMEM medium without serum. The cells culture medium was removed and the monolayers were washed with 2 ml of complete DMEM medium without serum. The diluted viruses were added to the wells of the culture plates (400 µl of viruses/well).

The infected cells were incubated during 1 hour at 35° C. and 5% $CO_2$ atmosphere, to allow the adsorption of the viral particles. After one hour of incubation, the monolayers were covered with complete DMEM culture medium, supplemented with 2% FBS and agarose with concentration of 20 mg/ml, hereafter named gelosed medium (4 ml of medium+agarose/well).

The cells were incubated during additional 72 hours, at 35° C. and 5% $CO_2$ atmosphere, when the cytopathic effect, characterized by occurrence of lysis plates in the monolayers, was observed. Independent clones of each of the viruses were captured, with help of a serologic pipette, by collecting a fragment of the gelosed medium above the lysis plates. The fragment of gelosed medium was placed into an Eppendorf tube containing complete DMEM medium supplemented with 2% FBS and stored at −80° C.

The above described cloning process was repeated more than once, from the agarose fragment obtained in the first cloning, and, after the second purification by lysis plate under agarose, the influenza viruses were amplified in liquid medium in MDCK cells. For this purpose, 500 µl of complete DMEM medium supplemented with 2% FBS, from the tube with the fragment of gelosed medium, were added to confluent monolayers of MDCK cells, in 25 cm2 culture flasks. The infected cells were incubated during 1 hour, at 35° C. and 5% $CO_2$ atmosphere to allow the adsorption of the viral particles. After one hour of incubation, the monolayers were covered with complete DMEM culture medium supplemented with 2.5% FBS. The cells were incubated during additional 72 hours, at 35° C. and 5% $CO_2$ atmosphere.

72 hours after infection, the supernatants of the cell cultures were collected and clarified by centrifugation, for 10 minutes, at 3,000 rpm and 4° C. The clarified supernatants were aliquoted and stored at −70° C., for latter quantification of the infectious titers.

For titrating the recombinant influenza viruses obtained by reverse genetics, MDCK cells were added to the wells of six-well culture plates, in a concentration of $8 \times 10^5$ cells per well and in 2 ml of complete DMEM medium supplemented with 5% FBS/well. The cells were incubated during additional 24 hours, at 35° C. and 5% $CO_2$ atmosphere. For infecting the cells, the viral stocks were subjected to serial decimal dilutions, in complete DMEM medium without serum. The cells culture medium was removed and the monolayers were washed with 2 ml of complete DMEM medium without serum. The diluted viruses were added to the wells of the culture plates (400 µl of viruses/well).

The infected cells were incubated during 1 hour at 35° C. and 5% $CO_2$ atmosphere, to allow the adsorption of the viral particles. After one hour of incubation, the monolayers were covered with gelosed medium (4 ml of medium+agarose/well).

The cells were incubated during additional 72 hours, at 35° C. and 5% $CO_2$ atmosphere, when the cytopathic effect was observed. The infectious titer was calculated by multiplying the number of lysis plates by the dilution factor and by the correction factor of 2.5. The results were presented as number of plate forming units (pfu) per ml of supernatant.

To analyze the expression of the SAG2 heterologous sequence by the vNA38-SAG2 virus, a northern blot assay was performed for detecting the molecular species carrying the SAG2 heterologous sequence (see FIG. 3A for more details). For this purpose, preferably MDCK cells were infected by the wild WSN virus, or one of the recombinant viruses with a M.O.I of 2. Twenty-four hours after infection, the total cellular RNA was extracted by use of Trizol™ reagent (Life Technologies), according to manufacturer's instructions. After denaturation at 70° C. in 50% formamide, 2.2M formaldehyde, 1×MOPS running buffer, 2 µg of RNA from each sample were analyzed in agarose gel, transferred to a nylon membrane (Hybond N, Amersham), and hybridized with a DNA probe labeled with $^{32}P$ specific for the SAG2 sequence, allowing detection of RNAs with negative (vRNAs) or positive (cRNAs, mRNAs) polarities. The RNA bands were evidenced after exposing the membrane in Biomax MR-1 Biofilm (Kodak) (FIG. 3B).

Figures 4A, 4B:
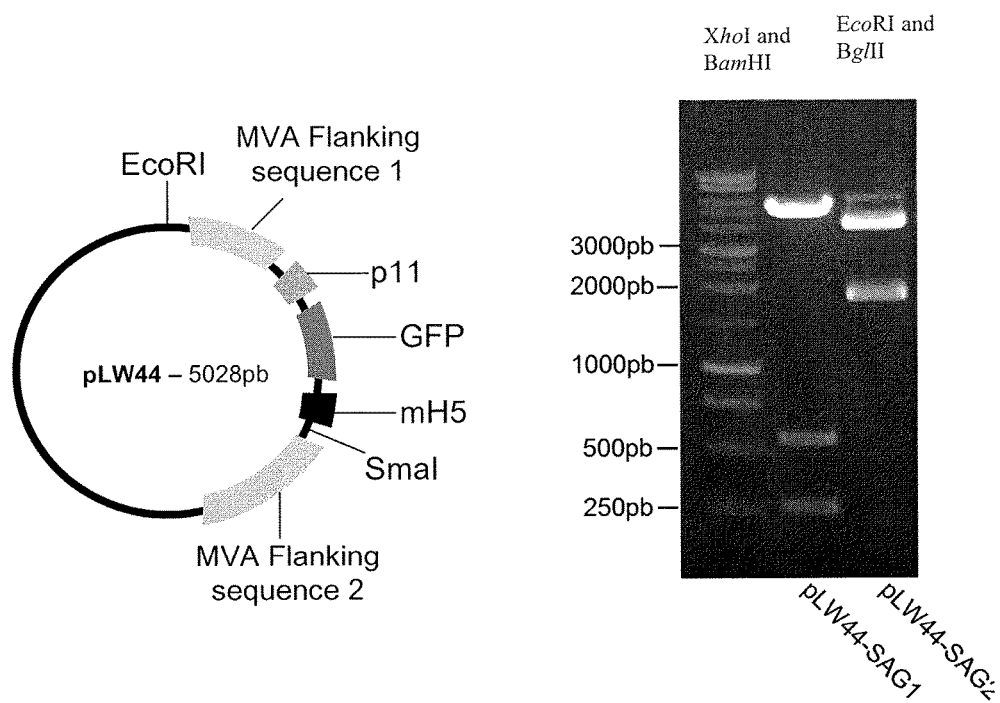
FIG. 4B shows the digestion profile of the pLW44-SAG1 and pLW44-SAG2 plasmids.
Figure 5:
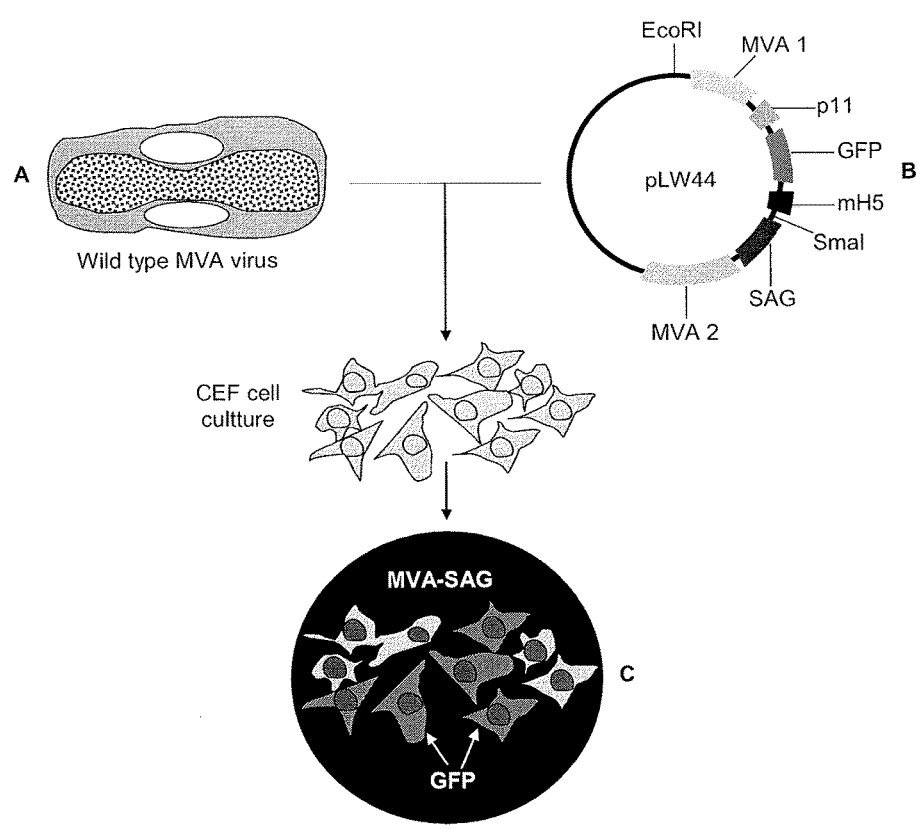
FIG. 5 shows the strategy of construction of the recombinant MVA viruses carrying the SAG1 or SAG2 sequences, by the homologous recombination technique.

FIG. 4 outlines the construction process of the plw44-SAG1 and plw44-SAG2 plasmids. The pLW44 plasmid (ceded by Dr. Bernard Moss, of the Laboratory of Viral Diseases, NIAID-NHI, EUA). The pLW44 plasmid has the GFP ("Green Fluorescent Protein") signaling gene under control of the p11 promoter ("Vaccinia virus late promoter") and an expression cassette adapted to eukaryotic cells, flanked by regions of homology to the MVA DNA.

FIG. 5 outlines the construction process of the recombinant MVA viruses by homologous recombination technique. The mentioned recombinant viruses' construction process comprises the stages:

- cloning of the *T. gondii* genes that encodes SAG1 or SAG2 proteins on the transfer vector p1w44;
- transfection of the pLW44-SAG1 or plw44-SAG2 plasmid and infection by a wild MVA virus;
- generation of the MVA viruses by homologous recombination;
- cloning and amplification of the recombinant viruses;
- characterization of the expression of the proteins of interest.

For generation of the recombinant MVAs, a culture of CEFs was infected with the wild MVA (A) and subsequently transfected with plasmid containing the transgene of interest (B). The homologous recombination between the viral genome and the expression cassette containing the transgene of interest was verified through the occurrence of fluorescence due to the reporter gene GFP (C) expression.

In the cloning stage (FIG. 4), the genes encoding the SAG1 or SAG2 proteins were obtained by digestion with the HindIII and BglII restriction enzymes, from the pAd-SAG1 and pAd-SAG2 plasmids respectively. The plw44 vector was digested with the restriction enzyme SmaI.

The digestion products were treated with the T4 DNA polymerase enzyme during 5 minutes at 37° C., to fill their ends not matched, which were formed by digestion with the restriction enzymes. The enzyme inactivation was performed during 10 minutes at 75° C.

The plw44 vector and the digestion fragments containing a encoding sequence of SAG1 or SAG2 protein were purified by electrophoresis in agarose gel, at nearly 1%, and the gel bands corresponding to each gene were eluted from gel fragments by using a commercial purification kit.

After the purification procedure, linking reactions were performed amongst the plw44 vector and the digestion reaction products, in order to maintain preferably an insert/plasmid molar ratio of 3:1, using for this purpose an appropriate enzyme as, for example, the T4-ligase enzyme, using preferably 10 units of enzyme per reaction, at approximately 16° C., for nearly 3 hours. The inserts obtained were added in the plw44 transfer vector on the SmaI site, under control of the mH5 promoter ("Vaccinia virus early/late promoter").

The products of the linking reaction were employed in *Escherichia coli* bacterium transformation. In the present concretization, the chemocompetent XLI-Blue strain of *Escherichia coli* bacterium was used.

The transformant bacteria were grown in appropriate culture containing an appropriate culture medium such as, for example, the LB medium. Approximately 100 μg/ml of ampicillin was added to the LB medium. Preferably, the mentioned culture occurred in a 16-18 hours period and the recombinant plasmids were purified with commercial plasmid isolation kits. The plasmids may alternatively be purified through alkaline lysis of the recombinant bacteria, with buffer containing sodium hydroxide and sodium dodecyl sulfate, followed by neutralization of bacterial lysate, with buffer composed of glacial acetic acid and potassium acetate, and subsequent filtration of lysate and precipitation of plasmids with 100% Ethanol.

The SAG1 and SAG2 genes were cloned in the pLW44 plasmid. The presence of the recombinant gene and its correct orientation in the plasmid were confirmed by observing the digestion profile of the purified plasmid (FIG. 4B).

For construction of the recombinant MVA viruses, procedure used in the present invention was the infection of the permissive cells with a Wild MVA viruses, followed by transfection with plw44-SAG1 or plw44-SAG2 plasmid. For generation of the recombinant MVA viruses carrying the SAG1 or SAG2 genes, the cells from primary cultures of chicken embryo fibroblasts (CEF) were initially infected with 0.1 M.O.I (multiplicity of infection) of wild MVA virus and, subsequently, transfected with the plw44-SAG1 or plw44-SAG2 plasmid, through Lipofectamine 2000 (GIBCO) reagent, which consists in a liposomes suspension.

For the cells transfection to occur, the execution of a first procedure was required for preparing the permissive cells. During this first procedure for permissive cells preparation as, for example, the CEF cells, the same were seeded preferably into six-well plates, in a density of approximately 500,000 cells/well. To each well were added nearly 2 ml/well of culture medium. Mentioned cells were cultured during nearly 24 hours, under a preferred temperature of 35° C., in an atmosphere with nearly 5% $CO_2$, of an appropriate culture medium as, for example, the DMEM medium, which was supplemented with approximately 5% fetal bovine serum, sodium bicarbonate in a preferred concentration of 5 mM, HEPES in a preferred concentration of 25 mM and nearly 40 mg/l of gentamicin. Mentioned culture medium is called complete EMEM medium.

Until the moment of infection and addition of the transfection reagents and the plasmids, the six-well plates containing washed monolayers were maintained in culture with nearly 2 ml/well of complete EMEM medium, at a preferred temperature of 35° C. and 5% $CO_2$ atmosphere.

For generation of the recombinant MVA viruses, the cells were first infected with 0.1 M.O.I of the wild MVA virus. Each infection was performed into an individual well of a six-well plate, containing a monolayer of nearly 500,000 cells and a confluence of nearly 90%.

Two hours after infection, the cells were transfected with the pLW44-SAG1 or plw44-SAG2 plasmid. For each transfection reaction, 3 μl of liposomes solution (Lipofectamine 2000) and 2 μg of the above mentioned plasmids were separately diluted into 50 μl of EMEM culture medium and incubated at room temperature during 20 minutes. The plasmid and liposomes solutions were then blended, incubated during 10 minutes and added to the cells.

After addition of the transfection reagent and the plasmids, the six-well plates containing the washed monolayers were maintained in culture with nearly 2 ml of complete EMEM medium supplemented with 10% FBS/well, at a preferred temperature of 35° C. and 5% $CO_2$ atmosphere, during 5 hours. After this time, the culture medium was removed and replaced by 2 ml of complete EMEM medium supplemented with 2.5% FBS/well. The cells were incubated during additional 48 hours, at 35° C. and 5% $CO_2$ atmosphere, when the extracts of the infected/transfected cells were collected and stored preferably at −70° C.

The selection of the recombinant MVA clones was performed 5 times, on six-well culture plates with $5 \times 10^5$ CEF cells/well. One aliquot of the material obtained after initial infection/transfection was serially diluted by a factor of 10, and used to infect the cultures. After 2 hours of incubation, 2 ml of EMEM, without pH indicator and added by 1% melted agarose, were added to each well. After the agarose solidification at room temperature, the plates were incubated at 35° C. and 5% $CO_2$ until development of fluorescence.

The presence of recombinant MVA in the CEF culture, after infection, was indicated by the occurrence of green fluorescence in the infected cells. Cultures showing few fluorescent cells, without confluence, were used for collection of MVA clones, by puncture and aspiration of agarose. The gel fragments were transferred to 0.5 ml of EMEM 2.5% FBS. 400 μl of each EMEM aliquot containing the MVA clones were used for infecting new plates containing CEF. The extracts of cells were collected 48 hours after the infection and used to infect new culture plates. After selection, the extracts obtained were used to expand the clones, in cultures with increasing numbers of cells, aiming to attain a titer of $10^9$ plate forming units (pfu)/ml of recombinant MVA viruses.

Figure 6:
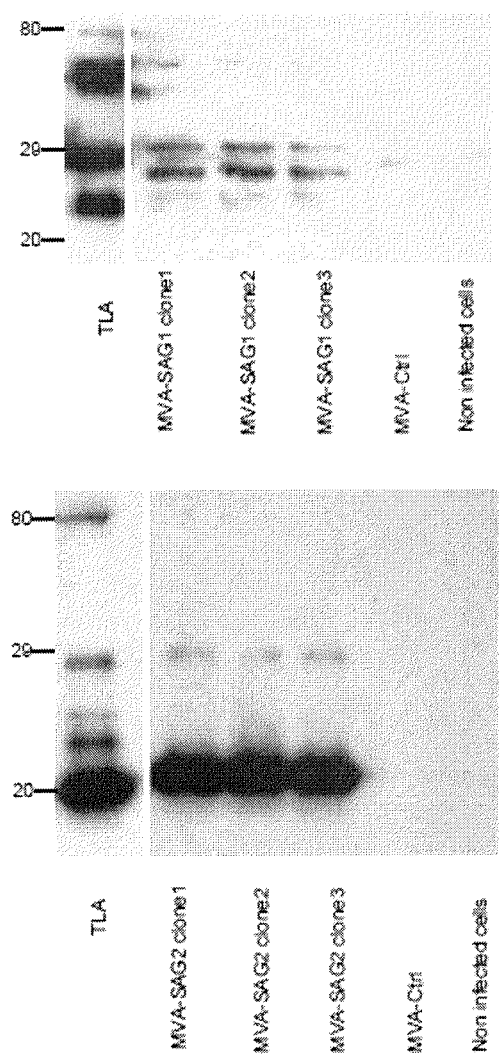
FIG. 6 shows the results of the experiment conducted using the Western blot technique for detecting SAG1 and SAG2 proteins in HEK 293A cells infected with the recombinant MVA viruses.

The expression of the SAG1 and SAG2 proteins by the recombinant MVA viruses was assessed "in vitro", through the "Western-blot" technique accomplished with the extract of permissive cells, infected CEF, against the sera of mice immunized with recombinant adenoviruses encoding the SAG1 or SAG2 protein. As shown in FIG. 6, it can be noticed that the viruses are able to induce the expression of unique proteins, SAG1 or SAG2, which promptly react with the serum of the immunized animal.

Next, the present invention will be described in detail through examples. It is necessary to emphasize that the invention is not limited to this example, but that it also includes changes and modifications within the limits in which it operates.

EXAMPLE 1

Evaluation of Immunogenic Capacity of Recombinant Influenza Viruses with the Gene of the *T. Gondii* SAG2 Protein, in BALB/c Mice The recombinant influenza virus with the gene of SAG2 protein (vNA38-SAG2) was subjected to an evaluation of its immunogenic capacity in BALB/c mice.

Figure 7:
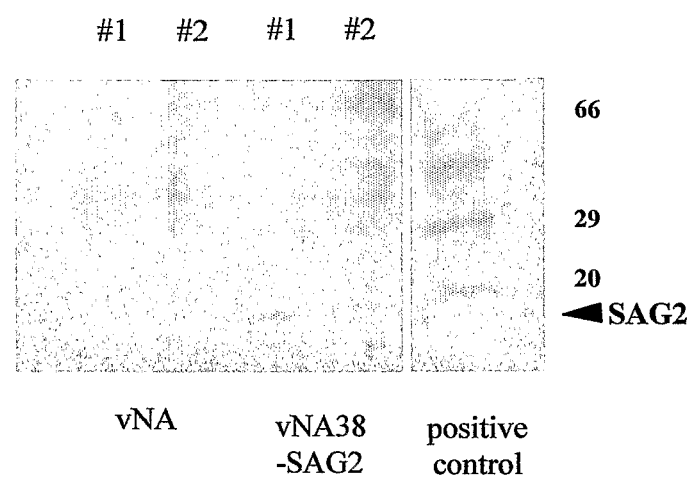
FIG. 7 shows the results of the experiment conducted using the Western blot technique for detecting anti-SAG2 antibodies in mice immunized with the recombinant influenza virus vNA38-SAG2.
Figure 8:
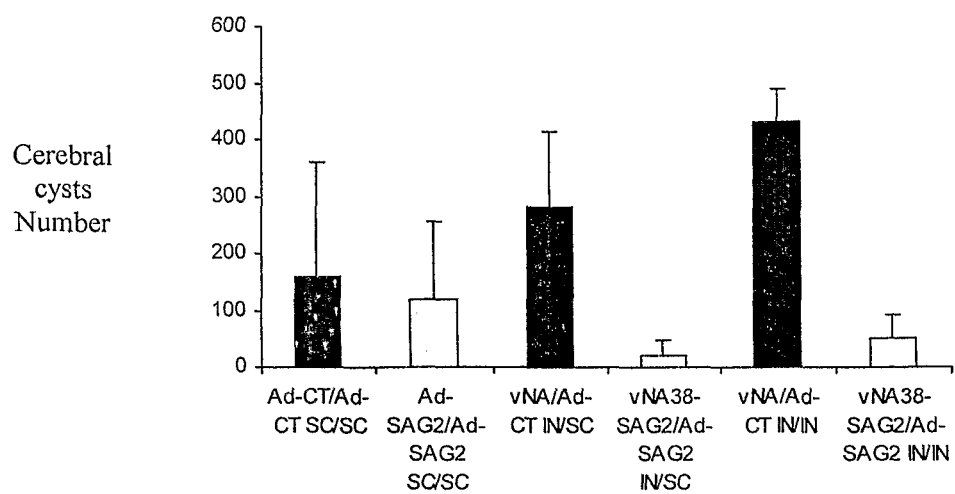
FIG. 8 shows the results of challenge experiments performed on mice immunized with recombinant viruses, according to different protocols, and experimentally infected with *T. gondii* PBR strain cysts.
Figure 10:
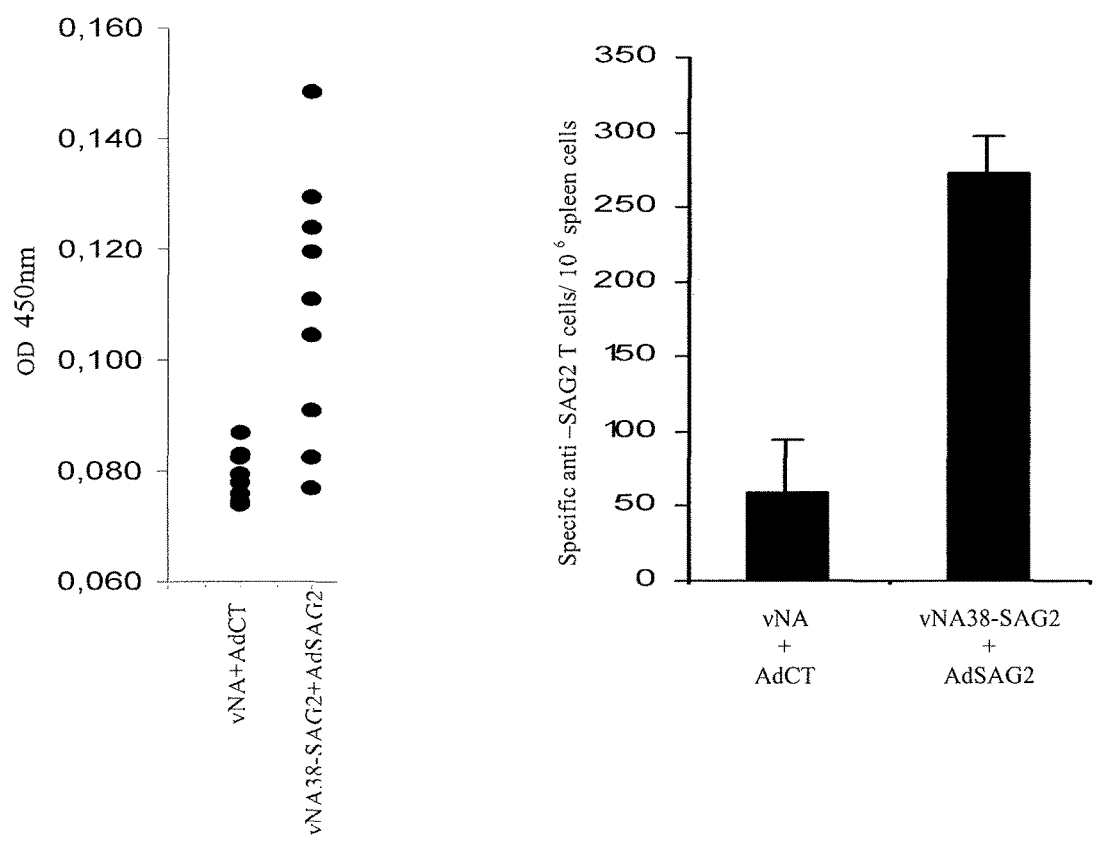
FIG. 10 shows the anti-SAG2 immune response in mice immunized according to the heterologous protocol of immune response induction and enhancement.

In the experiment shown in FIG. 7, preferential groups of 5 females with ages around 6-8 weeks received preferably an intranasal inoculation of nearly $10^3$ pfu of vNA38-SAG2 influenza virus or control virus (vNA).

The production of anti-SAG2 IgG antibodies was evaluated in serum samples obtained from bleeding held in BALB/c mice close to 21 days after immunization. For this purpose, the sera of the animals inoculated with the VNA or vNA38-SAG2 viruses were tested using the Western blot technique, against extracts of HEK293A cells infected with recombinant adenovirus carrying the SAG2 (rAdSAG2) sequence.

In results of the Western blot test, shown in FIG. 7, there is the presence of IgG antibodies of the sera from two animals immunized with vNA38-SAG2 front of the SAG2 antigens. The immunization with control influenza virus (vNA), on the other hand, did not induce the production of antibodies.

Additionally, the present invention describes a novel immunization protocol. Mentioned immunization protocol consists in the sequential utilization of influenza virus and recombinant adenovirus expressing the same heterologous antigen, in protocols of priming and boosting immune responses. Preferably, the recombinant influenza viruses are used for initial immunizations (prime), while the recombinant adenoviruses are used for strengthening immunizations (boost).

According to the present invention, the immunization protocol with recombinant viruses is as follows.

| | Immunization protocol | | |
|---|---|---|---|
| Group | Initial Immunization (Prime) | Strengthening Immunization (Boost) | Inoculation Route |
| 01 | mock | mock | xxx |
| 02 | vNA | Ad-CTL | in/sc |
| 03 | vNA38-SAG2 | Ad-SAG2 | in/sc |
| 04 | Ad-CTL | Ad-CTL | sc/sc |
| 05 | Ad-SAG2 | Ad-SAG2 | sc/sc |
| 06 | vNA | Ad-CTL | in/in |
| 07 | vNA38-SAG2 | Ad-SAG2 | in/in |

The protocol above illustrates an example of immunization scheme using recombinant adenovirus and influenza virus. In the example illustrated, 5 groups of preferably female BALE/c mice, with ages of 6-8, weeks were immunized with $10^3$ pfu of recombinant influenza virus (vNA38-SAG2) or the control, by intranasal route. Preferably, within a period of 02 to 04 weeks after the first immunization, the animals immunized with control influenza virus received a second immunization with $10^8$ pfu of control adenovirus (by subcutaneous or intranasal route), while the animals immunized with $10^3$ pfu of recombinant vNA38-SAG2 influenza virus received an boost immunization with $10^8$ pfu of rAd-SAG2 (by subcutaneous or intranasal route).

As a control, in the experiment illustrated in FIG. 8, a group of animals was subjected to two sequential immunizations of $10^8$ pfu of control adenovirus or rad-SAG2, by subcutaneous route, within a period of 4 weeks.

To evaluate the efficacy of this vaccination protocol, preferably 4 weeks after the second immunization, each of the animals subjected to the different immunization protocols received received a dose of 20 cysts of the *T. gondii* PER strain, by oral route. Eight weeks after the challenge, the number of cysts in the brain was quantified by optical microscopy.

As can be seen in FIG. 8, animals subjected to two sequential immunizations with rAd-SAG2 showed a reduction of nearly 25% on the number of brain cysts, when compared to the group of animals immunized twice with control adenovirus. On the other hand, a much more significant reduction, around 90%, was observed in animals that were prime-immunized with vNA38-SAG2 and subjected to an boost immunization with rAd-SAG2. This reduction was observed in both groups of animals immunized with recombinant adenovirus by subcutaneous route, as those immunized by intranasal route.

With the purpose of further illustrating the present invention advantages, different vaccination protocols using the SGA1 and SAG2 surface antigens expressed from the viral vectors, are presented below.

Protocol 1—Influenza Virus and Adenovirus Carrying the *T. gondii* SAG2 Antigen.

As previously described, different clones of recombinant influenza virus carrying the SAG2 antigens (vNA38-SAG2) were generated through the molecular biology technique known as reverse genetics. Such viruses proved to be able to express SAG2 in infected cells. Moreover, when used in heterologous protocols of immune response induction and enhancement, in association with recombinant adenoviruses carrying the SAG2 antigen (rAd-SAG2), it was possible to observe the reduction in the number of brain cysts.

1.1) Protection Assays

The heterologous protocol of immune response induction and enhancement using the recombinant influenza viruses and adenoviruses was more deeply studied throughout this year. For this purpose, female BALB/c mice, with age of nearly 8 weeks, were anesthetized with a mixture of ketamine and xylazine and subjected to an immunization with $10^3$ pfu/animal (approximately 0.1 DL50) of (vNA) wild virus or vNA38-SAG2, by intranasal route. Four weeks later, the animals were subjected to a boost immunization with $10^8$ pfu/animal of control adenovirus (rAd-Ctrl) or adenovirus carrying the SAG2 sequence (rAd-SAG2), by subcutaneous route. Alternately, for comparison, some animals were subjected to two immunizations with $10^8$ pfu/animal of rAd-CTrl or rAd-SAG2, by subcutaneous route, within an 8 weeks period.

Furthermore, aiming to confirm the hypothesis that two immunizations with recombinant viruses would be necessary for inducing a protective immune response, one group of animals was subjected to a single immunization with rAd-SAG2. Finally, aiming to exclude the possibility that the rule of the influenza virus, during the prime-immunization, would be just inducing the innate immune response through its own proteins and nucleic acid, and not the rule of inducing a specific anti-SAG2 immune response, some animals were subjected to a prime-immunization with control influenza virus (vNA), and to a boost immunization with rAd-SAG2.

As can be observed in FIG. 9, the animals subjected to two sequential immunizations with rAd-SAG2 presented a reduction of nearly 70% on the number of brain cysts, when compared to the group of animals immunized twice with control adenovirus. Comparable results were observed in animals that were prime-immunized with vNA38-SAG2 and subjected to a boost immunization with rAd-SAG2. In these cases, the reduction on the number of brain cysts was nearly 80%. Moreover, it is important emphasizing that the animals subjected to only a single immunization with rAd-SAG2 or with vNA+rAd−SAG2 presented a number of cysts comparable to that of the animals immunized with the control viruses. These results evidence that two immunizations are required for induction of a protective immune response, and that the recombinant influenza viruses are good candidates to be used in development of a vaccine against Toxoplasmosis.

1.2) Immune Response Mechanisms

Aiming to better elucidate the mechanisms involved in the protection of animals immunized with recombinant adenoviruses and influenza viruses, were conducted experiments in which female BALB/c mice, with age of approximately 8 weeks, were anesthetized with a mixture of ketamine and xylazine and subjected to an immunization with $10^3$ pfu/animal (nearly 0.1 LD50) of wild virus (VNA) or vNA38-SAG2, by intranasal route.

Four weeks later, the animals were subjected to a boost immunization with $10^8$ pfu/animal, by subcutaneous route, of control adenovirus (rAd-Ctrl) or rAd-SAG2. The presence of serum antibodies (IgG) in the vaccinated animals was analyzed 03 weeks after the boost immunization, using the ELISA technique and antigenic fraction 3 (F3) as capture antigen. As can be noticed in FIG. 10A, significant levels of antibodies could be detected in animals immunized with recombinant viruses carrying the SAG2 antigen. The presence of T lymphocytes producers of interferon gamma in the spleen of the immunized animals were examined by ELISPOT technique, using the antigen presenting cells stimulated with antigen F3. As can be noticed in FIG. 10B, in the spleen cells of animals immunized with recombinant viruses carrying the SAG2 antigen, it was possible to detect the presence of T cells specific for SAG2, producing interferon gamma.

1.3) Genetic Stability of the Recombinant Influenza Viruses and Multiplication in vivo The genetic stability of recombinant influenza viruses was evaluated both in cell culture and in mice. For this purpose, regarding the stability in cellular culture, it was analyzed the presence of the SAG2 insert in four SAG2 influenza virus stockpiles ($4^{th}$ passage after the reverse genetics). All the viruses retained the insert. Moreover, results obtained from the sequencing analysis had not showed any mutation in the SAG2 sequence of clones analyzed (data not shown).

With the objective of analyzing the genetic stability of recombinant influenza viruses in vivo, female BALB/c mice, with nearly 8 weeks of age, were anesthetized with a mixture of ketamine and xylazine and inoculated by intranasal route with $10^3$ pfu of influenza control virus (vNA) or vNA38-

Figure 11:
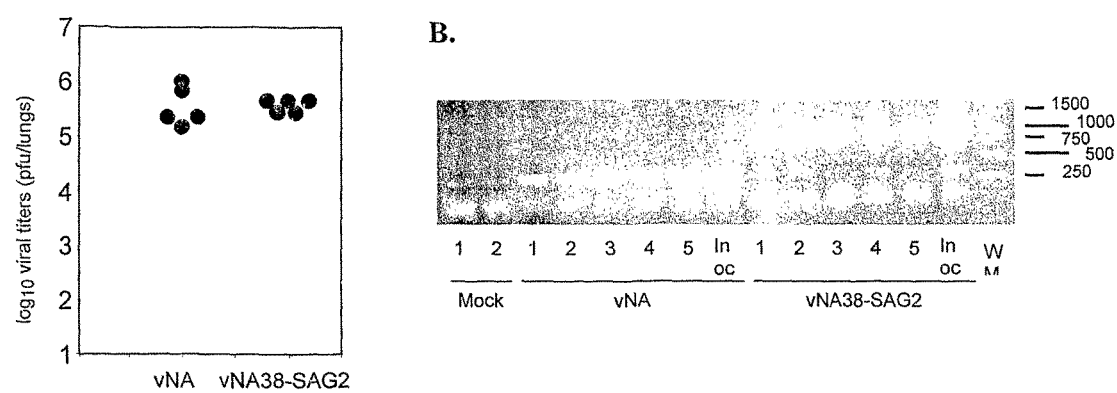
FIG. 11 shows a study on recombinant influenza viruses in mice.

SAG2. Five days after infection, the animals were sacrificed and the viral load in their lungs was analyzed by titration by lysis plate under agarose in MDCK cells. As can be noticed in FIG. 11A, the viral titers observed in the lungs of animals inoculated with the vNA38-SAG2 viruses were similar to those obtained with the control virus, demonstrating the ability of recombinant virus to multiply effectively in the lungs of infected animals. Finally, using the RT-PCR technique, it was analyzed the presence of the SAG2 insert, in the viruses obtained from lungs of infected animals. As shown in FIG. 11B, all samples retained the SAG2 insert, thus confirming the vNA38-SAG2 virus stability in vivo.

Protocol 2—Adenovirus and MVA Virus Carrying the *T. gondii* SAG1 or SAG2 Antigens.

This immunization protocol consists in the utilization of recombinant adenovirus and MVA viruses carrying the SAGs surface antigen.

2.1) Induction of Anti-SAG2 Heterospecific Immune Response and Protection Assays.

Figure 12:
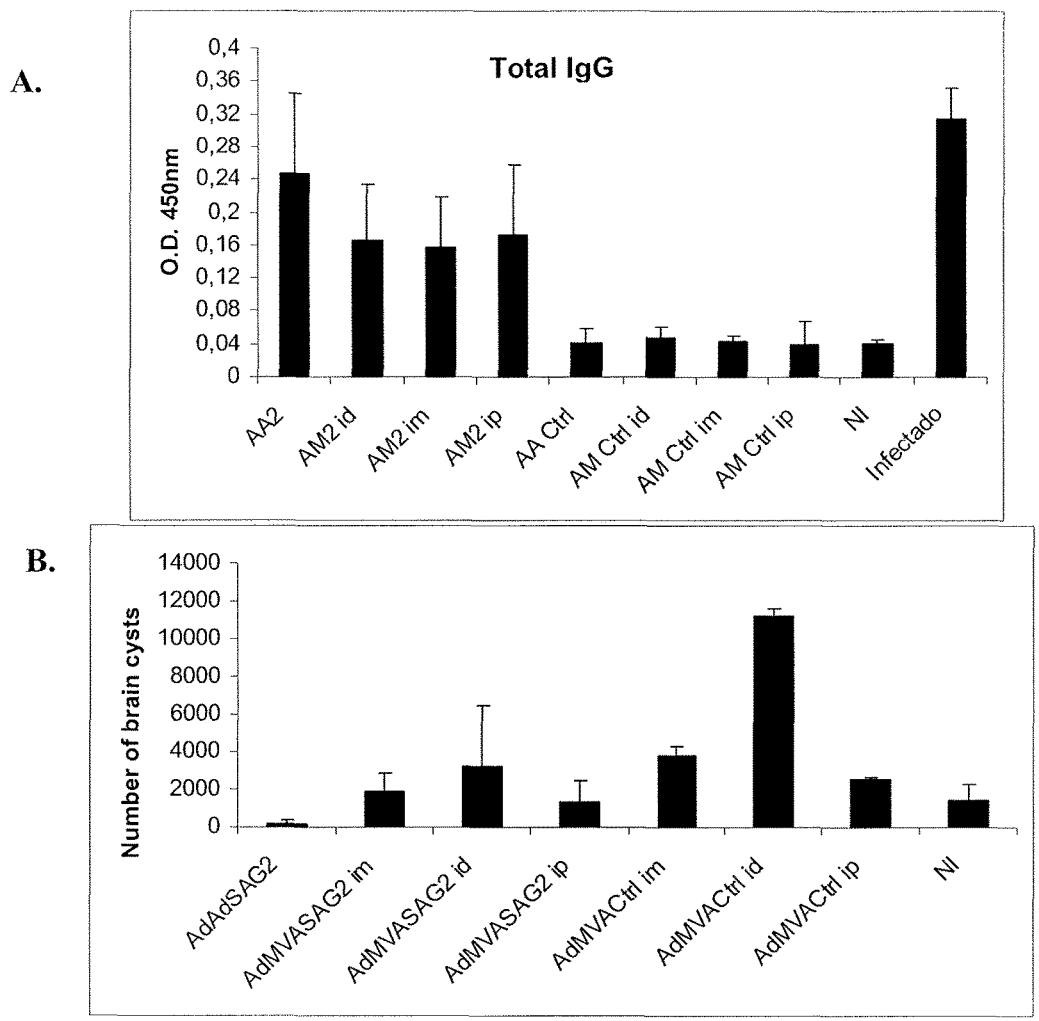
FIG. 12 shows the evaluation result on the heterologous protocol of immune response induction and enhancement, using adenovirus and MVA virus carrying the *T. gondii* SAG2 antigen.

Female BALB/c mice were immunized by subcutaneous route with $10^9$ pfu of adenovirus (Ad-SAG2 or control adenovirus). Four weeks after the prime-immunization, the animals were immunized with $10^7$ pfu of recombinant MVA viruses (MVA-SAG2 or MVA-Ctrl) by intraperitoneal route. Alternatively, the animals were anesthetized with a mixture of ketamine and xylazine, being then immunized with $10^7$ pfu of MVA viruses (MVA-SAG2 or control MVA) by intradermic route (the injections were made in the ears of animals) or by intramuscular route (the injections were applied to the front of both thighs of animals). For control, groups of animals were subjected to two immunizations with $10^9$ pfu of recombinant adenovirus (rAd-SAG2 or rAd-Ctrl) by subcutaneous route. Two weeks after the boost immunization, the animals serum was collected and the presence of serum antibodies (anti-SAG2) (IgG) in the vaccinated animals was analyzed, being used the antigenic fraction 3 (F3) as capture antigen. As can be observed in FIG. 12A, anti-SAG2 antibodies could be detected in the animals immunized with recombinant viruses carrying the SAG2 antigen. Furthermore, our results do not indicate any significant difference consequent of the inoculation route of the MVA viruses. The antibody titers obtained were lower than those observed in animals immunized according to the homologous protocol, notwithstanding only after performing statistical analyses, we will be able to investigate the significance level of these results. The capacity of this heterologous protocol in providing protection in face of infection by *T. gondii* was evaluated through the infection of immunized animals (2 weeks after the boost immunization) with 20 cysts of the PBr strain, by oral route. Forty-five days after the challenge, the animals were sacrificed and the number of brain cysts was counted by optical microscopy. As shown in FIG. 12B, our results indicate a protective effect from the immunization with recombinant adenovirus and MVA carrying the SAG2 antigen. Concerning the animals that were immunized with MVA-SAG2 by intradermic route, the reduction was nearly 50%, while a more significant reduction (~75%) was observed in animals that were immunized by intraperitoneal route.

2.2) Induction of Anti-SAG1 Heterospecific Immune Response and Protection Assays.

Figure 13:
FIG. 13 shows the induction of heterospecific humoral immune response in mice immunized with adenovirus and MVA viru carrying the *T. gondii* SAG1 antigen.
Figure 13:
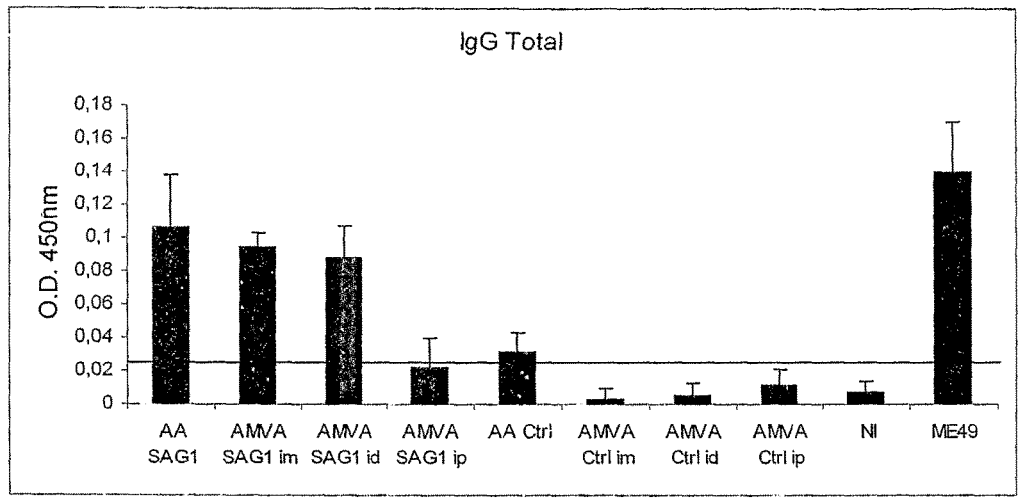

In these experiments, female C57BL/6 mice were immunized with recombinant viruses, according to the protocol described in the previous paragraph. Two weeks after the boost immunization, the animals were bled and the presence of serum anti-SAG2 antibodies (IgG) was analyzed by the Western blot technique, using the total extract (TLA) of the RH strain tachyzoites as capture antigen. As shown in FIG. 13A, exception made to the immunization with MVA viruses by intraperitoneal route, the vaccination in mice with adenovirus and MVA-SAG1 virus was able to induce anti-SAG1 antibodies. Furthermore, our results were comparable to those obtained when animals were subjected to two immunizations with rAd-SAG1. Moreover, these results were confirmed when the same sera were used in ELISA experiment. As observed in FIG. 13B, the immunization with rAd-SAG1 followed by immunization with MVA-SAG1, both by intramuscular route and by intradermic route, was able to induce significant levels of anti-SAG1 antibodies, comparable to those observed when animals were subjected to two immunizations with rAd-SAG1.

Figure 14:
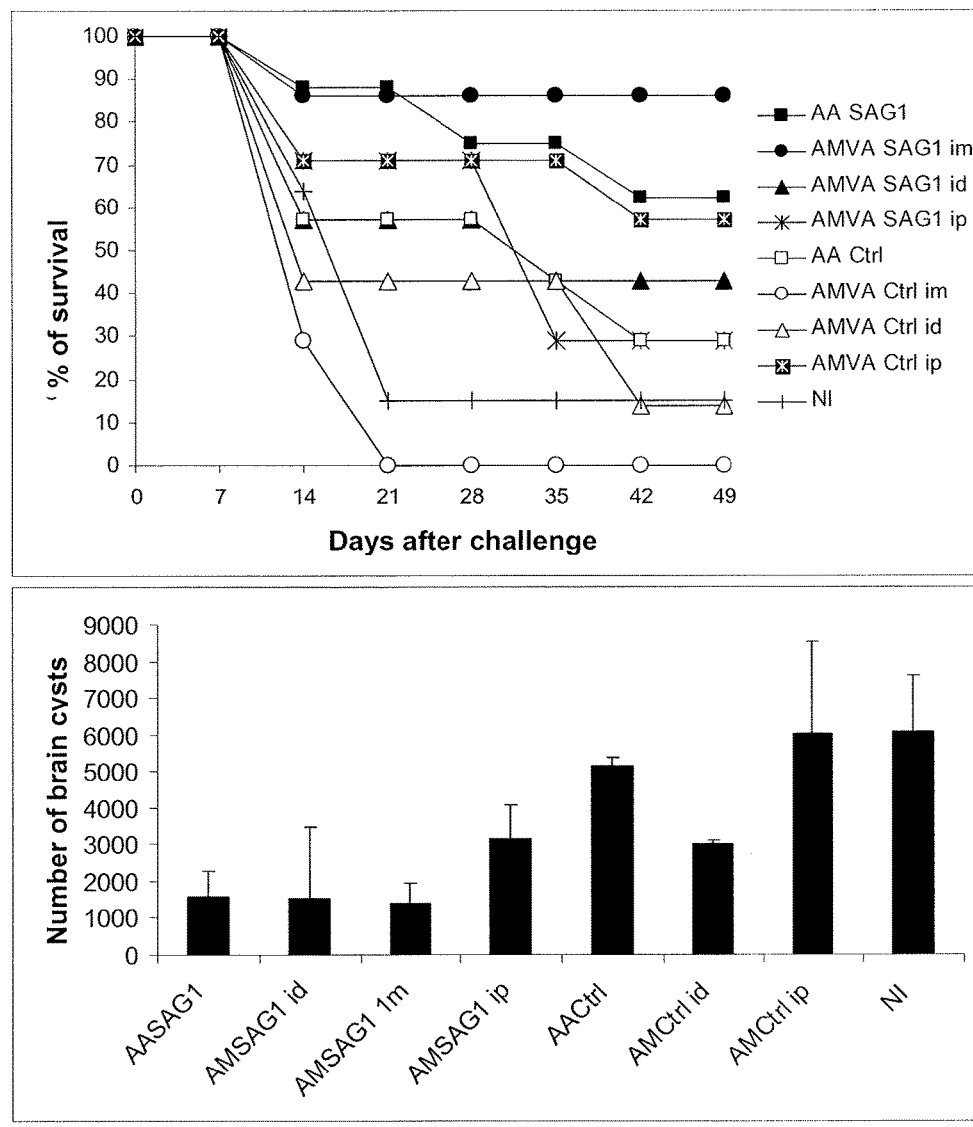
FIG. 14 shows the evaluation result on the heterologous protocol of immune response induction and enhancement, using adenovirus and MVA virus carrying the *T. gondii* SAG1 antigen.

The ability of the immunization with rAd–SAG2+MVA–SAG2 in protecting the vaccinated animals was assessed through the challenge infection with 10 cysts of the ME49 strain, by oral route, being the survival of animals followed during nearly 45 days. As can be noticed in FIG. 14A, the heterologous protocol, according to which the MVA-SAG1 virus was administered by intramuscular route, has resulted in better protection (90% survival versus 0% survival of animals in the control group). These results were also significantly better than those observed in animals immunized with two doses of rAd-SAG1. Animals that survived the challenge were sacrificed and the number of brain cysts was quantified by optical microscopy. As noticed in FIG. 14B, the animals immunized with recombinant viruses carrying the SAG1 antigen, according to the homologous or heterologous protocols, showed a reduction of nearly 50% on the number of brain cysts, when compared to their respective controls.

Protocol 3—Influenza Virus and MVA Virus Carrying the *T. gondil* SAG2 Antigen.

Figure 15:
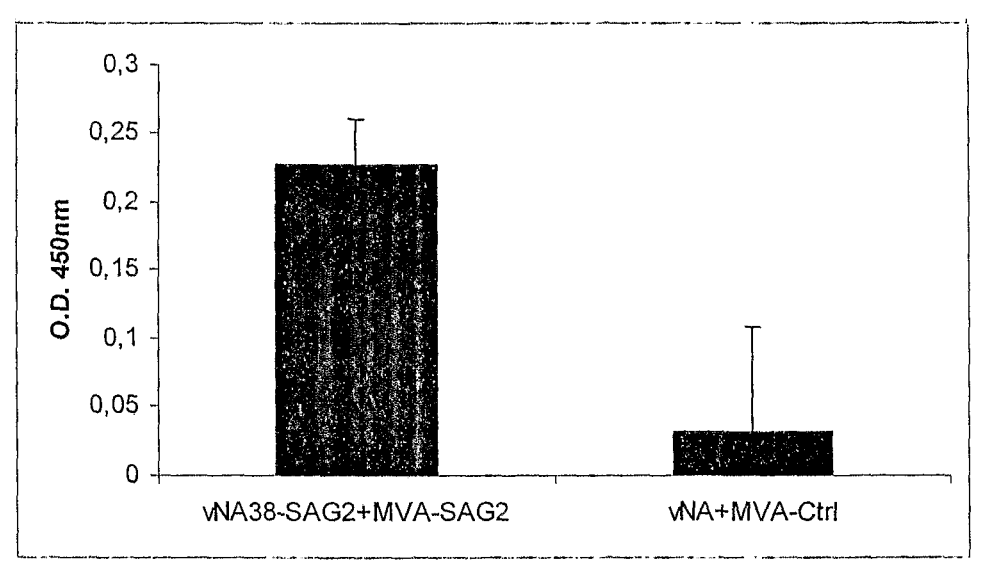

This immunization protocol consists in utilization of recombinant influenza virus and MVA virus carrying the SAG2 antigen. For this purpose, female BALBc mice, with age of 8 weeks, were immunized with influenza virus, as previously described in this report, and, four weeks later, the animals were anesthetized with a mixture of ketamine and xylazine, and received a boost dose of $10^7$ pfu of recombinant MVA virus, by intramuscular route. Two weeks after the boost immunization, the animals were bled and the antibody titers were evaluated by ELISA technique, being used the tachyzoites total antigen (TLA) as capture antigen. The results are shown in FIG. 15. As can be observed, these preliminary results show that the immunization with recombinant influenza and MVA virus carrying the SAG2 antigen were able to induce anti-SAG2 antibodies.

Thus, comprehensively, the results demonstrate the potential of the recombinant influenza, adenovirus and MVA viruses carrying the SAG antigens, in developing a vaccine against Toxoplasmosis.

The invention described herein and the aspects discussed herein shall be regarded as one of the possible concretizations. It must, however be clear that the invention is not limited to these concretizations, and those with the technical skill will realize that any particular feature introduced on it shall only be understood as something that was described to facilitate understanding and can not be made without departing from the inventive concept described. The limiting characteristics of the object of this invention are related to the claims included in this report.

The invention claimed is:

1. An immunogenic composition capable of inducing an immune response against Toxoplasmosis in a patient comprising the following immunogenic compositions, in combination:
   an initial immunization dose adapted for any inoculation route and comprising a recombinant influenza virus of any subtype comprising a vector carrying one or more viral segments that became bicistronic by duplication of a 3' non-encoding region and of nucleotides of a 5' encoding region of one or more viral segments, wherein the vector comprises a nucleic acid sequence encoding a sequence selected from the group consisting of the *T. gondii* SAG1 antigen, the *T. gondii* SAG2 antigen, and combinations thereof; and a booster immunization dose adapted for any inoculation route and comprising a recombinant adenovirus of any subtype which comprises a vector comprising a nucleic acid sequence encoding a sequence selected from the group consisting of the *T. gondii* SAG1 antigen, the *T. gondii* SAG2 antigen, and combinations thereof, wherein the immunogenic composition induces an immune response against Toxoplasmosis in the patient.

2. An immunogenic composition capable of inducing an immune response against Toxoplasmosis in a patient comprising the following immunogenic compositions, in combination:

an initial immunization dose adapted for any inoculation route comprising a recombinant adenovirus of any serotype and which comprises a vector comprising a nucleic acid sequence encoding a sequence selected from the group consisting of the *T. gondii* SAG1 antigen, the *T. gondii* SAG2 antigen, and combinations thereof; and a booster immunization dose adapted for any inoculation route and comprising a recombinant influenza virus of any subtype comprising a vector carrying one or more viral segments that became bicistronic by duplication of a 3' non-encoding region and of nucleotides of a 5' encoding region of one or more viral segments, wherein the vector comprises a nucleic acid sequence encoding a sequence selected from the group consisting of the *T. gondii* SAG1 antigen, the *T. gondii* SAG2 antigen, and combinations thereof, wherein the immunogenic composition induces an immune response against Toxoplasmosis in the patient.

3. The immunogenic composition of claim 1, wherein the vectors of the initial immunization and the booster immunization comprise a nucleic acid sequence encoding a sequence consisting of the *T. gondii* SAG2 antigen.

4. The immunogenic composition of claim 2, wherein the vectors of the initial immunization and the booster immunization comprise a nucleic acid sequence encoding a sequence consisting of the *T. gondii* SAG2 antigen.

5. The immunogenic composition of claim 1, wherein the vectors of the initial immunization and the booster immunization comprise a nucleic acid sequence encoding a sequence consisting of the *T. gondii* SAG1 antigen.

6. The immunogenic composition of claim 2, wherein the vectors of the initial immunization and the booster immunization comprise a nucleic acid sequence encoding a sequence consisting of the *T. gondii* SAG1 antigen.

* * * * *